(12) United States Patent
Aliprandi et al.

(10) Patent No.: US 10,689,671 B2
(45) Date of Patent: Jun. 23, 2020

(54) MICROORGANISM AND METHOD FOR THE PRODUCTION OF 1.2-PROPANEDIOL BASED ON NADPH DEPENDENT ACETOL REDUCTASE AND IMPROVED NADPH SUPPLY

(71) Applicant: METABOLIC EXPLORER, Saint Beauzire (FR)

(72) Inventors: Pascale Aliprandi, Surat (FR); Emilie Navarro, Villenave d' Ornon (FR); Céline Raynaud, Saint Beauzire (FR); Gwénaëlle Bestel Corre, Saint Beauzire (FR); Philippe Soucaille, Deyme (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 15/310,156

(22) PCT Filed: May 12, 2015

(86) PCT No.: PCT/EP2015/060487
§ 371 (c)(1),
(2) Date: Nov. 10, 2016

(87) PCT Pub. No.: WO2015/173247
PCT Pub. Date: Nov. 19, 2015

(65) Prior Publication Data
US 2017/0145446 A1  May 25, 2017

(30) Foreign Application Priority Data

May 12, 2014 (EP) .................................... 14305691

(51) Int. Cl.
| | | |
|---|---|---|
| *C12P 7/18* | (2006.01) | |
| *C12N 9/04* | (2006.01) | |
| *C12N 15/52* | (2006.01) | |
| *C12N 15/74* | (2006.01) | |

(52) U.S. Cl.
CPC .............. *C12P 7/18* (2013.01); *C12N 9/0006* (2013.01); *C12N 15/52* (2013.01); *C12N 15/74* (2013.01); *C12Y 101/01001* (2013.01)

(58) Field of Classification Search
None
See application file for complete search history.

(56) References Cited

U.S. PATENT DOCUMENTS

| | | |
|---|---|---|
| 2007/0072279 A1 | 3/2007 | Meynial-Salles et al. |
| 2007/0087403 A1 | 4/2007 | Bestel-Corre et al. |

FOREIGN PATENT DOCUMENTS

| | | |
|---|---|---|
| JP | 2007-510411 A | 4/2007 |
| WO | WO 01/07626 A2 | 2/2001 |
| WO | WO 2005/047498 A1 | 5/2005 |
| WO | WO 2005/073364 A2 | 8/2005 |
| WO | WO 2011/012697 A2 | 2/2011 |
| WO | WO-2013/052604 A1 * | 4/2013 |
| WO | WO 2014/026162 A1 | 2/2014 |

OTHER PUBLICATIONS

Chica et al., Semi-rational approaches to engineering enzyme activity: combining the benefits of directed evolution and rational design. Curr. Opi. Biotechnol., 2005, vol. 16: 378-384.*
Kisselev L., Polypeptide release factors in prokaryotes and eukaryotes: same function, different structure. Structure, 2002, vol. 10: 8-9.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kaneko et al. Sequence Analysis of the Genome of the Unicellular Cyanobacterium *Synechocystis* sp. Strain PCC6803. II. Sequence Determination of the Entire Genome and Assignment of Potential Protein-coding Regions. DNA Research 3, 109-136, 1996.*
Altaras et al., "Enhanced production of (R)-1,2-propanediol by metabolically engineered *Escherichia coli*," 2000 (published on web Aug. 25, 2000), Biotechnol. Prog., vol. 16, No. 6, pp. 940-946.
Altaras et al., "Metabolic Engineering of a 1,2-Propanediol Pathway in *Escherichia coli*," Mar. 1999, Appl. Environ. Microbial., vol. 65, No. 3, pp. 1180-1185.
Badía et al., "Fermentation mechanism of fucose and rhamnose in *Salmonella typhimurium* and *Klebsiella pneumoniae*," Jan. 1985, J. Bacterial., vol. 161, No. 1, pp. 435-437.
Berríos-Rivera et al., "The effect of carbon sources and lactate dehydrogenase deletion on 1,2-propanediol production in *Escherichia coli*," Jan. 2003, J. Ind. Microbial. Biotechnol., vol. 30, No. 1, pp. 34-40.
Bocanegra et al., "Creation of an NADP-dependent pyruvate dehydrogenase multienzyme complex by protein engineering," Mar. 23, 1993, Biochemistry, vol. 32, No. 11, pp. 2737-2740.
Cameron et al., "Metabolic engineering of propanediol pathways," 1998 (published on web Jan. 16, 1998), Biotechnol. Prog., vol. 14, No. 1, pp. 116-125.
Carrier et al., "Library of sysnthetic 5' secondary structures to manipulate mRNA stability in *Escherichia coli*," 1999 (published on web Jan. 9, 1999), Biotechnol Prog., vol. 15, No. 1, pp. 58-64.

(Continued)

*Primary Examiner* — Iqbal H Chowdhury

(74) *Attorney, Agent, or Firm* — Birch, Stewart, Kolasch & Birch, LLP

(57) ABSTRACT

The present invention relates to a recombinant microorganism useful for the production of 1,2-propanediol and process for the preparation of 1,2-propanediol. The microorganism of the invention is modified in a way that the 1,2-propanediol production is improved by enhancing NADPH dependent HAR activity.

13 Claims, No Drawings
Specification includes a Sequence Listing.

(56) References Cited

OTHER PUBLICATIONS

Centeno-Leija et al., "Metabolic and transcriptional response of *Escherichia coli* with a NADP$^+$-dependent glyceraldehyde 3-phosphate dehydrogenase from *Streptococcus* mutans," 2013 (published online Aug. 29, 2013), Antonie Van Leeuwenhoek, vol. 104, No. 6, pp. 913-924.

Clermont et al., "Determinants of coenzyme specificity in glyceraldehyde-3-phosphate dehydrogenase: Role of the acidic residue in the fingerprint region of the nucleotide binding fold," Sep. 1993, Biochemistry, vol. 32, No. 38, pp. 10178-10184.

Corbier et al., "Probing the coenzyme specificity of glyceraldehyde-3-phosphate dehydrogenases by site-directed mutagenesis," 1990, Biochemistry, vol. 29, No. 30, pp. 7101-7106.

Datsenko et al., "One-step Inactivation of Chromosomal Genes in *Escherichia coli* K-12 Using PCR Products," Jun. 6, 2000, PNAS, vol. 97, No. 12, pp. 6640-6645.

Dereeper et al., "Blast-Explorer helps you building datasets for phylogenetic analysis," 2010, BMC Evol Biol., vol. 10, No. 8, pp. 1-6.

Dereeper et al., "Phylogeny.fr: robust phylogenetic analysis for the non-specialist," 2008 (published online Apr. 19, 2008), Nucleic Acids Res., vol. 36, pp. W465-W469.

Fuhrer et al., "Different Biochemical Mechanisms Ensure Network-Wide Balancing of Reducing Equivalents in Microbial Metabolism," Apr. 2009 (published ahead of print on Jan. 30, 2009), J. Bacteriol., vol. 191, No. 7, pp. 2112-2121.

Hanai et al., "Engineered Synthetic Pathway for Isopropanol Production in *Escherichia coli*," Dec. 2007 (published ahead of print on Oct. 12, 2007), Appl. Environ. Microbial., vol. 73, No. 24, pp. 7814-7818.

Huang et al., "Characterization of Methylglyoxal Synthase from Clostridium acetobutylicum ATCC 824 and Its Use in the Formation of 1,2-Propanediol," Jul. 1999, Appl. Environ. Microbial., vol. 65, No. 7, pp. 3244-3247.

Ismaiel et al., "Purification and characterization of a primary-secondary alcohol dehydrogenase from two strains of *Clostridium beijerinckii*," Aug. 1993, J. Bacterial., vol. 175, No. 16, pp. 5097-5105.

Jarboe, "YqhD: a broad-substrate range aldehyde reductase with various applications in production of biorenewable fuels and chemicals," Applied Microbiology and Biotechnology, 2011 (published online Oct. 6, 2010), vol. 89, No. 2, pp. 249-257.

Katzberg et al., "Engineering Cofactor Preference of Ketone Reducing Biocatalysts: A Mutagenesis Study on a γ-Diketone Reductase from the Yeast *Saccharomyces cerevisiae* Serving as an Example," 2010 (published Apr. 14, 2010 ), Int. J. Mol. Sci., vol. 11, No. 4, pp. 1735-1758.

Kelley et al., "D-1-amino-2-propanol:NAD$^+$ oxidoreductase. Purification and general properties of the large molecular form of the enzyme from *Escherichia coli* K12," Feb. 25, 1984, J. Biol Chem., vol. 259, No. 4, pp. 2124-2129.

Lee et al., "Control of substrate access to the active site in methane monooxygenase," Feb. 21, 2013, Nature, vol. 494, No. 7437, pp. 380-384.

Li et al., "Engineering a cyanobacterium as the catalyst for the photosynthetic conversion of $CO_2$ to 1,2-propanediol," Microbial Cell Factories, Biomed Central, Jan. 22, 2013, vol. 12, No. 4, pp. 1-9.

Lim et al., "Amplification of the NADPH-related genes zwf and gnd for the oddball biosynthesis of PHB in an *E. coli* transformant harboring a cloned phbCAB operon," 2002, J Biosci Bioeng, vol. 93, No. 6, pp. 543-549.

Marbaix et al., "Extremely conserved ATP- or ADP-dependent enzymatic system for nicotinamide mucleotide repair," Dec. 2, 2011 (published online Oct. 12, 2011), J Biol Chem., vol. 286, No. 48, pp. 41246-41252 (18 pages).

Needleman et al., "A general method applicable to the search for similarities in the amino acid sequence of two proteins," Mar. 28, 1970, J. Mol. Biol., vol. 48, Issue 3, pp. 443-453.

Old et al., "In vitro expression of rat lens aldose reductase in *Escherichia coli*," Jul. 1, 1990, Proc. Natl. Acad. Sci. USA, vol. 87, No. 13, pp. 4942-4945.

Ruzheinikov et al., "Glycerol Dehydrogenase: Structure, Specificity, and Mechanism of a Family III Polyol Dehydrogenase," Sep. 2001, Structure, vol. 9, Issue 9, pp. 789-802.

Salis, "The Ribosome Binding Site Calculator," Dec. 2011, Methods in Enzymology, vol. 498, pp. 19-42 (25 pages).

Schmid et al., "Plasmid-mediated uptake and metabolism of sucrose by *Escherichia coli* K-12," Jul. 1982, J. Bacteriol., vol. 151, No. 1, pp. 68-76.

Scrutton et al., "Redesign of the coenzyme specificity of dehydrogenase by protein engineering," Jan. 4, 1990, Nature, vol. 343, pp. 38-43.

Segel, "Enzyme Kinetics: Behavior and Analysis of Rapid Equilibrium and Steady-State Enzyme Systems," 1993, John Wiley & Sons, pp. 44-54 and 100-113.

Wu et al., "Hidden Relationship between Conserved Residues and Locally Conserved Phosphate-Binding Structures in NAD(P)-Binding Proteins," 2012, J. Phys. Chem. B, vol. 116, No. 19, pp. 5644-5652.

Pakula et al., "Genetic Analysis of Protein Stability and Function", Annu. Rev. Genet., vol. 23, 1969, pp. 289-310.

* cited by examiner

SEQUENCE LISTING

```
<160> NUMBER OF SEQ ID NOS: 28

<210> SEQ ID NO 1
<211> LENGTH: 101
<212> TYPE: DNA
<213> ORGANISM: Artificial
<220> FEATURE:
<223> OTHER INFORMATION: Oligonucleotide for frdABCD

<400> SEQUENCE: 1
cgtgcaaacc tttcaagccg atcttgccat tgtaggcgcc ggtggcgcgg gattacgtgc      60
tgcaattgct gccgcgcagg ccatatgaat atcctcctta g                         101

<210> SEQ ID NO 2
<211> LENGTH: 100
<212> TYPE: DNA
<213> ORGANISM: Artificial
<220> FEATURE:
<223> OTHER INFORMATION: Oligonucleotide for frdABCD

<400> SEQUENCE: 2
cgttagattg taacgacacc aatcagcgtg acaactgtca ggatagcagc cagaccgtag      60
aaaacccatt tgcccgcagg tgtaggctgg agctgcttcg                           100

<210> SEQ ID NO 3
<211> LENGTH: 100
<212> TYPE: DNA
<213> ORGANISM: Artificial
<220> FEATURE:
<223> OTHER INFORMATION: Oligonucleotide for ptsG

<400> SEQUENCE: 3
atgtttaaga atgcatttgc taacctgcaa aaggtcggta atcgctgat gctgccggta       60 tccgtactgc ctatcgcagg tgtaggctgg agctgcttcg                           100

<210> SEQ ID NO 4
```

```
<211> LENGTH: 100
<212> TYPE: DNA
<213> ORGANISM: Artificial
<220> FEATURE:
<223> OTHER INFORMATION: Oligonucleotide for ptsG

<400> SEQUENCE: 4
ttagtggtta cggatgtact catccatctc ggttttcagg ttatcggatt tagtaccgaa      60
aatcgcctga acaccagaac catatgaata tcctccttag                           100

<210> SEQ ID NO 5
<211> LENGTH: 101
<212> TYPE: DNA
<213> ORGANISM: Artificial
<220> FEATURE:
<223> OTHER INFORMATION: Oligonucleotide for gldA

<400> SEQUENCE: 5
atggaccgca ttattcaatc accgggtaaa tacatccagg gcgctgatgt gattaatcgt      60
ctgggcgaat acctgaagcc gtgtaggctg gagctgcttc g                         101

<210> SEQ ID NO 6
<211> LENGTH: 100
<212> TYPE: DNA
<213> ORGANISM: Artificial
<220> FEATURE:
<223> OTHER INFORMATION: Oligonucleotide for gldA

<400> SEQUENCE: 6
ttattcccac tcttgcagga aacgctgacc gtactggtcg gctaccagca gagcggcgta      60
aacctgatct ggcgtcgcgc catatgaata tcctccttag                           100

<210> SEQ ID NO 7
<211> LENGTH: 21
<212> TYPE: DNA
<213> ORGANISM: Artificial
<220> FEATURE:
<223> OTHER INFORMATION: Ribosome binding site RBS120

<400> SEQUENCE: 7
atccggtata ggaggtatag a                                                21

<210> SEQ ID NO 8
<211> LENGTH: 261
<212> TYPE: DNA
<213> ORGANISM: Artificial
<220> FEATURE:
<223> OTHER INFORMATION: Sequence for recombination into pntAB

<400> SEQUENCE: 8
gaccgtcgaa gacaattatc agtctttatc cggcgttcta aggtgtttat cccactatca      60
cggctgaatc gttaatattt tgcgagttca cgccgaaata ctgattttg gcgctagatc     120 acaggcataa ttttcagtac gttatagggc gtttgttact aatttatttt aacggagtaa    180
catttagctc gtacatgagc agcttgtgtg gctcctgaca caggcaaacc atcatcaata    240
aaaccgatgg aagggaatat c                                              261

<210> SEQ ID NO 9
<211> LENGTH: 260
<212> TYPE: DNA
<213> ORGANISM: Artificial
<220> FEATURE:
<223> OTHER INFORMATION: Sequence for recombination into pntAB
```

<400> SEQUENCE: 9

```
atgcgaattg gcataccaag agaacggtta accaatgaaa cccgtgttgc agcaacgcca      60
aaaacagtgg aacagctgct gaaactgggt tttaccgtcg cggtagagag cggcgcgggt     120
caactggcaa gttttgacga taaagcgttt gtgcaagcgg cgctgaaat tgtagaaggg      180 aatagcgtct ggcagtcaga gatcattctg aaggtcaatg cgccgttaga tgatgaaatt     240
gcgttactga atcctgggac                                                 260
```

<210> SEQ ID NO 10
<211> LENGTH: 34
<212> TYPE: DNA
<213> ORGANISM: Artificial
<220> FEATURE:
<223> OTHER INFORMATION: Ribosome binding site RBS121

<400> SEQUENCE: 10

```
agacaataat cgaacaacat attaaggaga gttt                                  34
```

<210> SEQ ID NO 11
<211> LENGTH: 100
<212> TYPE: DNA
<213> ORGANISM: Artificial
<220> FEATURE:
<223> OTHER INFORMATION: oligonucleotides for Dgpi

<400> SEQUENCE: 11

```
ccaacgcaga ccgctgcctg gcaggcacta cagaaacact tcgatgaaat gaaagacgtt      60
acgatcgccg atcttttgc tgtaggctgg agctgcttcg                            100
```

<210> SEQ ID NO 12
<211> LENGTH: 100
<212> TYPE: DNA
<213> ORGANISM: Artificial
<220> FEATURE:
<223> OTHER INFORMATION: oligonucleotides for Dgpi

<400> SEQUENCE: 12

```
gcgccacgct ttatagcggt taatcagacc attggtcgag ctatcgtggc tgctgatttc      60
tttatcatct ttcagctctg catatgaata tcctccttag                           100
```

<210> SEQ ID NO 13
<211> LENGTH: 101
<212> TYPE: DNA
<213> ORGANISM: Artificial
<220> FEATURE:
<223> OTHER INFORMATION: Oligonucleotide for pfkA

<400> SEQUENCE: 13

```
gttcctcggt tctgcgcgtt tcccggaatt ccgcgacgag aacatccgcg ccgtggctat      60
cgaaaacctg aaaaaacgtg gtgtaggctg gagctgcttc g                        101
```

<210> SEQ ID NO 14
<211> LENGTH: 102
<212> TYPE: DNA
<213> ORGANISM: Artificial
<220> FEATURE:
<223> OTHER INFORMATION: Oligonucleotide for pfkA

<400> SEQUENCE: 14

```
ggcctgataa gcgaagcgca tcaggcattt ttgcttctgt catcggtttc agggtaaagg      60
```

```
aatctgcctt tttccgaaat cacatatgaa tatcctcctt ag                    102
```

<210> SEQ ID NO 15
<211> LENGTH: 81
<212> TYPE: DNA
<213> ORGANISM: Artificial
<220> FEATURE:
<223> OTHER INFORMATION: oligonucleotides for recombination into Pfka

<400> SEQUENCE: 15

```
gttcctcggt tctgcgcgtt tcccggaatt ccgcgacgag aacatccgcg ccgtggctat    60
cgaaaacctg aaaaaacgtg g                                              81
```

<210> SEQ ID NO 16
<211> LENGTH: 82
<212> TYPE: DNA
<213> ORGANISM: Artificial
<220> FEATURE:
<223> OTHER INFORMATION: oligonucleotides for recombination into Pfka

<400> SEQUENCE: 16

```
ggcctgataa gcgaagcgca tcaggcattt ttgcttctgt catcggtttc agggtaaagg    60
aatctgcctt tttccgaaat ca                                             82
```

<210> SEQ ID NO 17
<211> LENGTH: 28
<212> TYPE: DNA
<213> ORGANISM: Artificial
<220> FEATURE:
<223> OTHER INFORMATION: Ribosome binding site RBS113

<400> SEQUENCE: 17

```
aactcatttc gttttagggg aggaataa                                       28
```

<210> SEQ ID NO 18
<211> LENGTH: 202
<212> TYPE: DNA
<213> ORGANISM: Artificial
<220> FEATURE:
<223> OTHER INFORMATION: Sequence for recombination into ykiA

<400> SEQUENCE: 18

```
cttcccctyg aacgggaggg cattttyctg aaatatcctt tctttagccc ataataatat    60
ttcctttgct gcgattttttt caatttccga tatattcata atttatcaag gttgatataa   120
atatcagtga agatctccag atattgttgc ggaactggct acgataaaag ataaatcaga   180
tgatgaatgg tggcgtgcat tg                                            202
```

<210> SEQ ID NO 19
<211> LENGTH: 254
<212> TYPE: DNA
<213> ORGANISM: Artificial
<220> FEATURE:
<223> OTHER INFORMATION: Sequence for recombination into ykiA

<400> SEQUENCE: 19

```
catcctgatg actggtgaac tgcagcgtt aattcaaaac ctgattgaag gattaggtgg     60
cgaagcacaa cgttaattgc tgattttcct ttaatgccgg atgcgacgcc tgccgcgtct   120
tatccggcgt acgaagccac accaggcata taattattcg ctacggcgag caataattttt  180 tagcgcagca atattatgcg ttttacgctg taacttgctc catggacgtt gtgtcattgt   240
ttttcctcaa gccg                                                     254
```

<210> SEQ ID NO 20
<211> LENGTH: 100
<212> TYPE: DNA
<213> ORGANISM: Artificial
<220> FEATURE:
<223> OTHER INFORMATION: Oligonucleotide for lpd

<400> SEQUENCE: 20

```
atgagtactg aaatcaaaac tcaggtcgtg gtacttgggg caggccccgc aggttactcc      60
gctgccttcc gttgcgctga catatgaata tcctccttag                          100
```

<210> SEQ ID NO 21
<211> LENGTH: 100
<212> TYPE: DNA
<213> ORGANISM: Artificial
<220> FEATURE:
<223> OTHER INFORMATION: Oligonucleotide for lpd

<400> SEQUENCE: 21

```
ttacttcttc ttcgctttcg ggttcggcag gtcggtaatg ctaccttcga acacttctgc      60
cgccaggccc acagactcgt tgtaggctgg agctgcttcg                          100
```

<210> SEQ ID NO 22
<211> LENGTH: 33
<212> TYPE: DNA
<213> ORGANISM: Artificial
<220> FEATURE:
<223> OTHER INFORMATION: Ribosome binding site RBS131

<400> SEQUENCE: 22

```
tggcaaggta agcaaactat aaggaggtca aat                                  33
```

<210> SEQ ID NO 23
<211> LENGTH: 1013
<212> TYPE: DNA
<213> ORGANISM: Artificial
<220> FEATURE:
<223> OTHER INFORMATION: Synthetic gene gld

<400> SEQUENCE: 23

```
aagctttgat ggcaagcgat accattcgta ttccgggtat tgatacaccg ctgagccgtg      60
ttgcactggg cacctgggca attggtggtt ggatgtgggg tggtccggat gatgataatg     120
gtgttcgtac cattcatgca gcactggatg aaggtattaa tctgattgat accgctccgg     180
tttatggttt tggtcatagc gaagaaattg ttggtcgtgc actggcagaa aaaccgaata     240
aagcacatgt tgcaaccaaa ctgggtctgc attgggttgg tgaagatgag aaaaacatga     300
aagtgtttcg tgatagccgt ccggcacgta ttcgtaaaga agttgaagat agcctgcgtc     360
gtctgcgtgt tgaaaccatt gatctggaac aaattcattg gcctgatgat aaaccccga     420
ttgatgaaag cgcacgtgaa ctgcagaaac tgcatcagga tggtaaaatt cgtgccctgg     480
gtgttagcaa ttttagtccg gaacaaatgg atatctttcg tgaagttgca ccgctggcaa     540
ccattcagcc tccgctgaac ctgtttgaac gtaccattga aaaagatatt ctgccgtatg     600
ccgaaaaaca taatgcagtt gttctggcat atggtgcact gtgtcgtggt ctgctgaccg     660
gcaaaatgaa tcgtgatacc acctttccga agatgatct gcgtagcaat gatccgaaat     720
ttcagaaacc gaacttcgag aaatatctgg ctgcaatgga tgagtttgaa aaactggccg     780
agaaacgtgg taaaagcgtt atggcatttg cagttcgttg ggttctggat cagggtccgg     840
```

```
ttattgcact gtggggtgca cgtaaaccgg gtcaggttag cggtgttaaa gatgttttg      900
gttggagcct gaccgacgaa gaaaaaaaag cagttgatga tattctggca cgtcatgttc    960
cgaatccgat tgatccgacc tttatggcac cgcctgcacg tgattaagaa ttc          1013
```

<210> SEQ ID NO 24
<211> LENGTH: 971
<212> TYPE: DNA
<213> ORGANISM: Artificial
<220> FEATURE:
<223> OTHER INFORMATION: Synthetic gene gld2

<400> SEQUENCE: 24

```
aagctttgat ggcctccaag acgtacactc tgaacaccgg tgccaagata cccgcggtcg     60
ggttcggcac attcgccaat gagggtgcca agggcgagac atacgcagct gttacaaagg    120
cactggacgt tggataccgc caccttgatt gcgcgtggtt ttaccacaac gaagatgagg    180
ttggtgacgc ggtacgcgat tttctcgccc gccgacccga cgtgaaacgc gaggatctct    240
tcatttgcac caaagtttgg aaccacctgc atgagccaga ggacgtcaag tggagcgcca    300
agaactcgtg cgaaaacctc aaggtcgatt acattgacct gttcctcgtc cactggccaa    360
tcgcggccga agaacagc gacaggagcg tcaagctggg ccccgatggc aagtatgtca    420
tcaaccaagc cctgacggaa acccagagc caacatggcg agccatgaa gagcttgttg    480
aaagcggcct cgtcaaggca attggagtat ccaactggac gattccgggg ttgaagaagc    540
tccttcagat cgccaagatc aagccggcag tgaaccagat tgagattcac ccattcctac    600
caaacgaaga gcttgtggcg ttctgctttg agaacgggga cctgcccgaa gcctactcgc    660
cgctgggctc gcagaaccag gtcccaagca ccggcgagcg agtgcgcgac aacccgacac    720
tcaaagcggt tgccgagcga agcggctaca gccttgccca gatcctattg gcatggggcc    780
tgaagcgagg atatgtggtc ctcccaaaga gctcaactcc aagccgtatt gaaagcaact    840
tcaacattcc ggagctgagt gatgaagact ttgaggcgat tcaacaggtt gctaagggga    900
gacatactag atttgtcaac atgaaggaca cgtttggata caacgtttgg ccagaggagg    960
aataagaatt c                                                          971
```

<210> SEQ ID NO 25
<211> LENGTH: 1103
<212> TYPE: DNA
<213> ORGANISM: Artificial
<220> FEATURE:
<223> OTHER INFORMATION: Synthetic gene adh1

<400> SEQUENCE: 25

```
aagctttgac tagtatgaaa ggacttgcta tgcttggaat tggaagaatt ggatggattg     60
aaaagaaaat cccagaatgt ggaccacttg atgcattagt tagaccatta gcacttgcac    120
catgtacatc agatacacat accgtttggg caggagctat ggagataga catgatatga    180
ttcttggaca tgaagcggtt ggacaaattg ttaaagttgg atcattagtt aagagattaa    240
aagttggaga taaagttatt gtaccagcta ttacaccaga ttggggagaa gaagaatcgc    300
aaagaggata ccaatgcat tcaggaggaa tgcttggagg atggaaattc tcaaatttca    360
aggatggagt tttttcagaa gttttccatg ttaatgaagc agatgccaat cttgcacttc    420
ttccaagaga tattaaacca gaagatgcag ttatgttatc agatatggta actactggat    480
tccatgggagc agaattagct aatattaaac ttggagatac tgtttgtgtt attggtattg    540
gaccagttgg attaatgtca gttgcaggag caaaccatct tggagcagga agaatctttg    600
```

```
cagtaggatc aagaaaacat tgttgtgata ttgcattgga atatggagca acagatatta    660
ttaattataa aaatggagat attgtagaac aaattcttaa agctacagac ggcaaaggag    720
ttgataaagt cgttattgca ggaggtgatg ttcatacatt tgcacaagca gtcaaaatga    780
ttaaaccagg atcagatatt ggaaatgtta attatcttgg agaaggagat aatattgata    840
ttccaagaag tgaatgggga gttggaatgg tcataaaaca cattcatgga ggtttaaccc    900
caggtggaag agtcagaatg gaaaaattag catcacttat ttcaactggt aaattagata    960
cttctaaact tattacacat agatttgaag gattagaaaa agttgaagat gcattaatgt   1020
taatgaagaa taaaccagca gaccttatca aaccagttgt cagaattcat tatgatgatg   1080
aagatactct tcattaactc gag                                            1103
```

<210> SEQ ID NO 26
<211> LENGTH: 101
<212> TYPE: DNA
<213> ORGANISM: Artificial
<220> FEATURE:
<223> OTHER INFORMATION: Oligonucleotide for yqhDE

<400> SEQUENCE: 26

```
atgaacaact ttaatctgca cacccccaacc cgcattctgt ttggtaaagg cgcaatcgct    60
ggtttacgcg aacaaattcc gtgtaggctg gagctgcttc g                       101
```

<210> SEQ ID NO 27
<211> LENGTH: 99
<212> TYPE: DNA
<213> ORGANISM: Artificial
<220> FEATURE:
<223> OTHER INFORMATION: Oligonucleotide for yqhDE

<400> SEQUENCE: 27

```
ttagccgccg aactggtcag gatcgggacc gagacgcttg ccctgatcga gttttgcaat    60
ttcgccgagt tcgtctttgc atatgaatat cctccttag                           99
```

<210> SEQ ID NO 28
<211> LENGTH: 367
<212> TYPE: PRT
<213> ORGANISM: Escherichia coli

<400> SEQUENCE: 28

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

```
Val Ile Tyr Thr Asp Glu Gly Glu Phe Asp Arg Tyr Leu Leu Leu Pro
    130             135             140

Asn Asn Pro Asn Met Val Ile Val Asp Thr Lys Ile Val Ala Gly Ala
145             150             155             160

Pro Ala Arg Leu Leu Ala Ala Gly Ile Gly Asp Ala Leu Ala Thr Trp
            165             170             175

Phe Glu Ala Arg Ala Cys Ser Arg Ser Gly Ala Thr Thr Met Ala Gly
            180             185             190

Gly Lys Cys Thr Gln Ala Ala Leu Ala Leu Ala Glu Leu Cys Tyr Asn
        195             200             205

Thr Leu Leu Glu Glu Gly Glu Lys Ala Met Leu Ala Ala Glu Gln His
    210             215             220

Val Val Thr Pro Ala Leu Glu Arg Val Ile Glu Ala Asn Thr Tyr Leu
225             230             235             240

Ser Gly Val Gly Phe Glu Ser Gly Gly Leu Ala Ala Ala His Ala Val
                245             250             255

His Asn Gly Leu Thr Ala Ile Pro Asp Ala His His Tyr Tyr His Gly
            260             265             270

Glu Lys Val Ala Phe Gly Thr Leu Thr Gln Leu Val Leu Glu Asn Ala
        275             280             285

Pro Val Glu Glu Ile Glu Thr Val Ala Ala Leu Ser His Ala Val Gly
    290             295             300

Leu Pro Ile Thr Leu Ala Gln Leu Asp Ile Lys Glu Asp Val Pro Ala
305             310             315             320

Lys Met Arg Ile Val Ala Glu Ala Ala Cys Ala Glu Gly Glu Thr Ile
            325             330             335

His Asn Met Pro Gly Gly Ala Thr Pro Asp Gln Val Tyr Ala Ala Leu
            340             345             350

Leu Val Ala Asp Gln Tyr Gly Gln Arg Phe Leu Gln Glu Trp Glu
            355             360             365
```

MICROORGANISM AND METHOD FOR THE PRODUCTION OF 1.2-PROPANEDIOL BASED ON NADPH DEPENDENT ACETOL REDUCTASE AND IMPROVED NADPH SUPPLY

FIELD OF THE INVENTION

The present invention relates to a recombinant microorganism useful for the production of 1,2-propanediol and process for the preparation of 1,2-propanediol. The microorganism of the invention is modified in a way that the 1,2-propanediol production is improved by enhancing NADPH dependent acetol reductase activity.

BACKGROUND OF THE INVENTION 1,2-propanediol or propylene glycol, a C3 di-alcohol with formula $C_3H_8O_2$ or $HO-CH_2-CHOH-CH_3$, is a widely-used chemical. Its CAS number is 57-55-6. It is a colorless, nearly odorless, clear, viscous liquid with a faintly sweet taste, hygroscopic and miscible with water, acetone, and chloroform. It is a component of unsaturated polyester resins, liquid detergents, coolants, anti-freeze and de-icing fluids for aircrafts. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water, uses highly toxic substances and generates by-products such as tert-butanol and 1-phenyl ethanol.

The disadvantages of the chemical processes for the production of 1,2-propanediol make biological synthesis an attractive alternative. Two routes have been characterized for the fermentative production of 1,2-propanediol from sugars by microorganisms.

In the first route, 6-deoxy sugars (e.g. L-rhamnose or L-fucose) are cleaved into dihydroxyacetone phosphate and (S)-lactaldehyde, which can be further reduced to (S)-1,2-propanediol (Badia et al., 1985). This route is functional in *E. coli*, but can not yield an economically feasible process due to the elevated cost of the deoxyhexoses.

The second route is the metabolism of common sugars (e.g. glucose or xylose) through the glycolysis pathway followed by the methylglyoxal pathway. Dihydroxyacetone phosphate is converted to methylglyoxal that can be reduced either to lactaldehyde or to hydroxyacetone (acetol). These two compounds are then transformed into 1,2-propanediol. This route is used by natural producers of (R)-1,2-propanediol, such as *Clostridium sphenoides* and *Thermoanaerobacter thermosaccharolyticum*. However, improvement of the performances obtained with these organisms is likely to be limited due to the lack of available genetic tools.

PRIOR ART

The methylglyoxal pathway is functional in *E. coli* or other *Enterobacteriaceae* and several investigations for genetic modifications of *E. coli* in order to obtain a 1,2-propanediol producer using simple carbon sources have been led (WO 98/37204; Cameron et al., 1998; Altaras and Cameron, 1999; Huang et al., 1999; Altaras and Cameron, 2000; Berrios-Rivera et al., 2003; Jarboe, 2011). Improved 1,2-propanediol producing *E. coli* strains obtained by a combination of rational design and evolution are described in patent applications WO 2005/073364, WO 2008/116848, WO 2008/116852, WO 2008/116853, WO 2010/051849, WO 2011/012693, WO 2011/012697 and WO 2011/012702, which are hereby included per reference.

In *E. coli* 1,2-propanediol producing strains, the reduction of hydroxyacetone to 1,2-propanediol is carried out by the glycerol dehydrogenase GlyDH using NADH as a cofactor and is not total due to the internal redox state of the cell under aerobic conditions. Aerobically, the primary role of NADH is respiratory ATP generation via oxidative phosphorylation and as a result of this, the NADH-to-NAD+ ratio is strongly in favour of NAD+. The chemically very similar NADPH, in contrast, drives anabolic reductions, and the NADPH-to-NADP+ ratio is higher (Fuhrer and Sauer, 2009).

Therefore it is an object of the invention to improve the production of 1,2-propanediol by increasing NADPH dependent acetol reductase activity and by improving NADPH supply.

A three-dimensional structure of GlyDH from the thermophilic bacterium *Bacillus stearothermophilus* has been established and the NAD+ binding site was fully characterized (Ruzheinikov et al., 2001). A *B. stearothermophilus* mutant glyceraldehyde-3-phosphate able to produce NADPH has been constructed and characterized (Clermont et al., 1993).

The NADPH dependent secondary alcohol dehydrogenase (Sadh) from *Clostridium beijerinckii* naturally catalyzes the reduction of acetone to isopropanol (Ismaiel et al., 1993). In patent application EP2546331 from Mitsui Chemicals Inc. isopropyl alcohol is produced in an *E. coli* strain expressing sadh gene from *Clostridium beijerinckii*.

This enzyme as well as its homologue from *Thermoanaerobacter brockii* have been shown to catalyze the reduction of hydroxyacetone to 1,2-propanediol and were overexpressed in the obligate photoautotroph cyanobacterium *Synechococcus elongatus* to produce 1,2-propanediol from the non-carbohydrate $CO_2$ as carbon source (Li and Liao, 2013).

Unexpectedly, inventors have found that overexpression of sadh gene alone or in combination with other means to improve NADPH supply significantly improves 1,2-propanediol production from carbohydrates as carbon source.

SUMMARY OF THE INVENTION

The invention relates to recombinant microorganisms and methods using said microorganism for optimising the production of 1,2-propanediol, wherein in said microorganism the NADPH dependent acetol reductase (HAR) activity is enhanced. More particularly, in said recombinant microorganism, at least one gene coding for a NADPH dependent acetol reductase activity or a mutant gene gldA* coding for a NADPH dependent glycerol dehydrogenase is overexpressed, wherein said NADPH dependent acetol reductase has at least 60% amino acids identity with protein encoded by the adh gene from *Clostridium beijerinckii* or the adh gene from *Thermoanaerobacter brockii* or the adh1 gene from *Entamoeba histolytica* or the GOX1615 gene from *Gluconobacter oxydans* or the gld2 gene from *Hypocrea jecorina* or the yhdN gene from *Bacillus subtilis*.

The recombinant microorganism used in this invention may also comprise other genetic modifications such as:
  attenuated expression of gldA gene coding for a NADH dependent glycerol dehydrogenase,
  attenuated expression of yqhD gene coding for an aldehyde reductase, increased expression of pntAB gene operon coding for a nicotinamide nucleotide transhydrogenase, attenuated expression of pgi gene coding for a phosphoglucose isomerase, attenuated expression of pfkA gene coding for a phosphofructokinase, increased expression of zwf gene coding for a glucose-6-phosphate dehydrogenase, increased expression of yjeF gene coding for an ADP-dependent dehydratase, increased expression of gapN gene coding for a NADP-dependent glyceraldehyde-3-phosphate dehydrogenase, increased expression of lpd* mutant gene coding for a NADP-dependent lipoamide dehydrogenase.

Preferably the microorganism is *Escherichia coli*, *Klebsiella pneumoniae*, *Thermoanaerobacterium thermosaccharolyticum*, *Clostridium sphenoides* or *Saccharomyces cerevisiae*.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The present invention is related to a method for the production of 1,2-propanediol in a fermentative process comprising the steps of culturing a microorganism genetically modified for the production of 1,2-propanediol in an appropriate culture medium comprising a carbohydrate as source of carbon and recovering 1,2-propanediol from the culture medium, wherein the NADPH dependent HAR activity is enhanced in said genetically modified microorganism. Particularly preferred embodiments of the invention are further described below.

The terms "acetol reductase" and "hydroxyacetone reductase" or "HAR" are used interchangeably and denote enzymatic activity of reduction of acetol (or hydroxyacetone) into 1,2-propanediol. This activity may be NADPH dependent or NADH dependent.

The term "microorganism", as used herein, refers to a bacterium, yeast or fungus which is not modified artificially. Preferentially, the microorganism is selected among *Enterobacteriaceae*, *Bacillaceae*, *Clostridiaceae*, *Streptomycetaceae* and yeast. More preferentially the microorganism is a species of *Escherichia*, *Klebsiella*, *Thermoanaerobacterium*, *Clostridium* or *Saccharomyces*. Even more preferentially the microorganism is selected among *Escherichia coli*, *Klebsiella pneumoniae*, *Thermoanaerobacterium thermosaccharolyticum*, *Clostridium sphenoides* or *Saccharomyces cerevisiae*. Preferentially, the microorganism is a heterotroph microorganism, i.e. is not capable of fixing atmospheric carbon and uses instead organic carbon sources for its growth. Even more preferably, the heterotroph microorganism of the invention is *Escherichia coli*.

The term "recombinant microorganism" or "genetically modified microorganism", as used herein, refers to a bacterium, yeast or fungus that is not found in nature and is genetically different from its equivalent found in nature. It means, it is modified either by introduction or by deletion or by modification of genetic elements. It can also be transformed by forcing the development and evolution of new metabolic pathways by combining directed mutagenesis and evolution under specific selection pressure (see, for example, WO2005/073364 or WO2008/116852).

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

In contrast, "exogenous gene" means that the gene was introduced into a microorganism, by means well known by the man skilled in the art whereas this gene is not naturally occurring in the microorganism. Exogenous genes may be integrated into the host chromosome, or be expressed extrachromosomally by plasmids or vectors. A variety of plasmids, which differ with respect to their origin of replication and their copy number in the cell, are well known in the art. These genes may be homologous. "Overexpression" or "overexpressing" is also used to designate expression of exogenous genes in the microorganisms.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term 'functional homolog" for the purpose of the present invention relates to the fact that a certain enzymatic activity may not only be provided by a specific protein of defined amino acid sequence, but also by proteins of similar sequence from other (un)related microorganisms.

Using the references given in Uniprot for known protein or in Genbank for known genes, those skilled in the art are able to obtain protein and/or gene sequences and to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

According to the invention, the terms "fermentative process', 'fermentation" or 'culture' are used interchangeably to denote the growth of microorganism. This growth is generally conducted in fermenters with an appropriate growth medium adapted to the microorganism being used.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "source of carbon", "carbon source" or "carbon substrate" according to the present invention refers to any carbon source capable of being metabolized by a microorganism wherein the substrate contains at least one carbon atom.

The term "carbohydrate" refers to any carbon source capable of being metabolized by a microorganism and containing at least one carbon atom, two atoms of hydrogen and one atom of oxygen. $CO_2$ is not a carbohydrate because it does not contain hydrogen.

The carbohydrate is selected among the group consisting of monosaccharides such as glucose, fructose, mannose, xylose, arabinose, galactose and the like, disaccharides such as sucrose, cellobiose, maltose, lactose and the like, oligosaccharides such as raffinose, stachyose, maltodextrins and the like, polysaccharides such as cellulose, hemicellulose, starch and the like, methanol, formaldehyde and glycerol. Especially preferred carbon sources are arabinose, fructose, galactose, glucose, lactose, maltose, sucrose, xylose or a mixture thereof. More preferably carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

Those skilled in the art are able to define the culture conditions for the microorganisms according to the invention. In particular the bacteria are fermented at a temperature between 20° C. and 55° C., preferentially between 25° C. and 40° C., and more specifically about 30° C. to 37° C. for *E. coli*.

This process can be carried out either in a batch process, in a fed-batch process or in a continuous process. It can be carried out under aerobic, micro-aerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The phrase "recovering 1,2-propanediol from the culture medium" designates the process of purifying the produced 1,2-propanediol, using methods known by the man skilled in the art. Such methods are disclosed especially in patent applications WO2011/076690 and WO2012/130316.

The terms "microorganism genetically modified for the production of 1,2-propanediol" refer to microorganisms modified through either the introduction or deletion of genetic elements, or through a step of evolution as described in patent application WO 2005/073364. In particular, it designates a genetically modified microorganism presenting an improved 1,2-propanediol production in comparison with the endogenous production of the corresponding wild-type microorganism, without genetic modifications. Such microorganism is for example described in the patent application WO 2008/116848, WO 2008/116853, WO 2011/012693, WO 2011/012697, WO 2011/012702 or EP2532751 incorporated by reference. Preferred genetic modifications are the following:

increased expression of at least one gene selected among mgsA gene encoding methylglyoxal synthase, yqhD, yafB, ycdW, yqhE, yeaE, yghZ, yajO, tas, ydjG or ydbC genes encoding methylglyoxal reductase, gldA gene encoding glycerol dehydrogenase and fucO gene encoding lactaldehyde reductase;

deletion of either the edd gene encoding phosphphogluconate dehydratase or eda gene encoding 2-keto-3-deoxygluconate 6-phosphate aldolase or both;

attenuation of the synthesis of unwanted by-products by deletion of the genes coding for enzymes involved in synthesis of lactate from methylglyoxal (such as gloA gene encoding glyoxalase I, aldA gene encoding aldehyde dehydrogenase A, aldB gene encoding acetaldehyde dehydrogenase), lactate from pyruvate (ldhA gene encoding lactate dehydrogenase), formate (pflA gene encoding pyrvate formate lyase, pflB gene encoding pyruvate formate lyase), ethanol (adhE gene encoding aldehyde-alcohol dehydrogenase) and acetate (ackA gene encoding acetate kinase, pta gene encoding phosphate acetyltransferase, poxB gene encoding pyruvate oxidase);

elimination of the pathways consuming PEP like pyruvates kinases (encoded by the pykA and pykF genes) and/or by promoting the synthesis of PEP e.g. by overexpressing the ppsA gene coding for PEP synthase;

specific mutation in the lpd gene encoding lipoamide dehydrogenase;

the arcA gene encoding ArcA transcriptional dual regulator and the ndh gene encoding NADH:ubiquinone oxidoreductase II can be deleted, the gapA gene encoding glyceraldehyde 3-phosphate dehydrogenase is under the control of temperature inducible promoter, genes involved in the importation and metabolism of sucrose (cscB gene encoding sucrose permease, cscA gene encoding sucrose hydrolase, cscK gene encoding fructokinase, scrA gene encoding Enzyme II of the phosphoenolpyruvate-dependent phosphotransferase system, scrK gene encoding ATP-dependent fructokinase, scrB gene encoding sucrose 6-phosphate hydrolase (invertase), scrY gene encoding sucrose porine) are added or their expression is increased.

A preferred genetic modification is the improvement of methylglyoxal reductase activity, obtained by an increased expression of the gene yqhD*(G149E).

Another preferred genetic modification is the improvement of methylglyoxal synthase activity, obtained by an increased expression of the gene mgsA*(H21Q).

Another preferred genetic modification is the improvement of hydroxyacetone reductase activity, obtained by an increased expression of the gene gldA*(A160T). This HAR mutant is NADH dependent unlike the HAR mutant NADPH dependent disclosed hereinafter.

Hydroxyacetone reductase (HAR) is the last enzyme involved in the production of 1,2-propanediol. HAR catalyzes the following reaction:

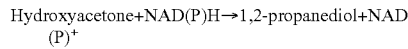

Hydroxyacetone+NAD(P)H→1,2-propanediol+NAD(P)⁺

A 1,2-propanediol producing strain wherein the gldA gene is deleted is not able to produce 1,2-propanediol anymore and accumulates hydroxyacetone (WO2008/116851). The GldA protein has been purified to homogeneity and uses NADH as a cofactor (Kelley and Dekker, 1984). In aerobic conditions, the conversion of hydroxyacetone to 1,2-propanediol is not total due to the internal redox state of the cell: under such conditions, the primary role of NADH is respiratory ATP generation via oxidative phosphorylation and as a result of this, the NADH-to-NAD+ ratio is strongly in favour of NAD+. The chemically very similar NADPH, in contrast, drives anabolic reductions, and the NADPH-to-NADP+ ratio is higher (Fuhrer and Sauer, 2009).

Following this observation, the object of this invention is to improve the production of 1,2-propanediol by increasing NADPH dependent hydroxyacetone reductase activity.

Increasing an activity can be obtained by improving the protein catalytic efficiency or decreasing protein turnover or decreasing messenger RNA (mRNA) turnover or increasing transcription of the gene or increasing translation of the mRNA.

Improving the protein catalytic efficiency means increasing the kcat and/or decreasing the Km for a given substrate and/or a given cofactor, and/or increasing the Ki for a given inhibitor. kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Mutations can be introduced by site-directed mutagenesis by usual methods like Polymerase Chain Reaction (PCR), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR). Stabilizing the protein can also be achieved by adding a peptide sequence called "tag" either at the N-terminus or the C-terminus of the protein. Tags are well known from the man skilled in the art. For instance, a Glutathione-S-Transferase (GST) can be used to stabilize a protein.

Decreasing mRNA turnover can be achieved by modifying the gene sequence of the 5'-untranslated region (5'-UTR) and/or the coding region, and/or the 3'-UTR (Carrier and Keasling, 1999).

Increasing transcription of a gene can be achieved by increasing the number of copies of the gene and/or using a promoter leading to a higher level of expression of the gene. "Overexpression" or "overexpressing" is also used to designate increasing transcription of a gene in the microorganisms.

For increasing the number of copies of the gene in the microorganism, the gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (e.g. for *E. coli* pSC101, RK2), low copy number plasmids (e.g. for *E. coli* pACYC, pRSF1010) or high copy number plasmids (e.g. for *E. coli* pSK bluescript II).

For using a promoter leading to a high level of expression of the gene the man skilled in the art knows which promoters are the most convenient, for example promoters Ptrc, Ptac, Plac, or the lambda promoter cI are widely used. These promoters can be "inducible" by a particular compound or by specific external condition like temperature or light. These promoters may be homologous or heterologous.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, proportionally alter its production rate, and control its activity inside the cell. The same RBS sequence will not have the same impact according to the nature of the mRNA. It is possible to optimize the strength of a RBS sequence to achieve a targeted translation initiation rate by using the software RBS CALCULATOR (Salis, 2011).

In a first aspect of the present invention, the production of 1,2-propanediol is improved by enhancing NADPH dependent acetol reductase (NADPH HAR) activity in the modified microorganism.

In a first embodiment of the invention, NADPH HAR activity is enhanced by overexpressing a gene encoding a NADPH HAR (NADPH HAR gene) in the modified microorganism.

Adh from *Clostridium beijerinckii* naturally catalyzes the reduction of acetone to isopropanol (Ismaiel et al., 1993). This enzyme as well as its homologue from *Thermoanaerobacter brockii* have been shown to catalyze the reduction of hydroxyacetone to 1,2-propanediol and were overexpressed in the obligate photoautotroph cyanobacterium *Synechococcus elongatus* to produce 1,2-propanediol from $CO_2$ as carbon source (Li and Liao, 2013).

Data mining and sequence analysis have been used to determine some candidate homologous enzymes and genes coding for such enzymes. These candidates are disclosed in Table 1 below.

The means of identifying homologous sequences and their percentage homologies are well known to those skilled in the art, and include in particular the BLAST programs. The sequences obtained can then be exploited (e.g., aligned) using, for example, the programs CLUSTALW or MULTALIN. Another way to identify protein homologues is through the construction of phylogenetic trees, using bioinformatics programs well known by the man skilled in the art.

TABLE 1

Possible candidates for NADPH dependent HAR enzymes:

| Organism | Function | UNIPROT |
| --- | --- | --- |
| *Mycoplasma pneumoniae* | NADP-dependent isopropanol dehydrogenase | P75214 |
| *Entamoeba histolytica* | NADP-dependent isopropanol dehydrogenase | P35630 |
| *Gadus callarias* | Probable NADP-dependent isopropanol dehydrogenase | P26325 |
| *Photobacterium damselae* | NADP-dependent isopropanol dehydrogenase | P39450 |
| *Synechocystis* sp | Alcohol dehydrogenase 1 | P73138 |
| *Oryza sativa* | S-(hydroxymethyl)glutathione dehydrogenase | Q4R1E8 |
| *Hordeum vulgare* | S-(hydroxymethyl)glutathione dehydrogenase | P10848 |
| *Sparus aurata* | Alcohol dehydrogenase 2 | P79896 |
| *Aspergillus nidulans* | NADP(+)-dependent glycerol dehydrogenase | Q7Z8L1 |
| *Gadus morhua* | Alcohol dehydrogenase 3 | P81600 |
| *Hordeum vulgare* | Alcohol dehydrogenase class-3 | P10847 |
| *Zea mays* | Alcohol dehydrogenase class-3 chain H | P04707 |
| *Trichomonas vaginalis* | NADP-dependent alcohol dehydrogenase, putative | A2EU60 |
| *Saccharomyces cerevisiae* | Alcohol dehydrogenase 2 | P38230 |
| *Pennisetum glaucum* | Alcohol dehydrogenase 2 | P14219 |
| *Oryctolagus cuniculus* | Probable quinone oxidoreductase | O46650 |
| *Arabidopsis thaliana* | Alcohol dehydrogenase 1 | Q0V7W6 |
| *Uromastyx hardwickii* | Alcohol dehydrogenase class-2 isozyme 2 | P25405 |
| *Amycolatopsis methanolica* | Alcohol dehydrogenase-like 5 | P80094 |
| *Zea luxurians* | Alcohol dehydrogenase 1A | Q07264 |
| *Gluconobacter oxydans* | Aldehyde reductase | Q5FQJ0 |
| *Zea mays* | S-(hydroxymethyl)mycothiol dehydrogenase | P00333 |
| *Oryctolagus cuniculus* | Alcohol dehydrogenase 1 | O46649 |
| *Arabidopsis thaliana* | Alcohol dehydrogenase 1 | P06525 |
| *Arabidopsis thaliana* | Alcohol dehydrogenase class-2 isozyme 1 | Q8LEB2 |
| *Cupriavidus necator* | Alcohol dehydrogenase class-P | P14940 |
| *Rana perezi* | Alcohol dehydrogenase-like 6 | P22797 |
| *Arabidopsis thaliana* | Alcohol dehydrogenase | Q9SK87 |
| *Rattus norvegicus* | Alcohol dehydrogenase 1 | Q64563 |
| *Malus domestica* | Alcohol dehydrogenase-like 2 | P48977 |
| *Saccharomyces_cerevisiae* | Glycerol 2-dehydrogenase (NADP(+)) | P14065 |
| *Drosophila melanogaster* | Alcohol dehydrogenase 4 | P46415 |
| *Mus musculus* | Alcohol dehydrogenase | Q9QYY9 |
| *Homo sapiens* | Alcohol dehydrogenase class-3 | P08319 |
| *Bacillus subtilis* | Alcohol dehydrogenase 4 | O31776 |
| *Peromyscus maniculatus* | Alcohol dehydrogenase 4 | P41681 |
| *Hansenula polymorpha* | Glycerol dehydrogenase | Q6BC32 |
| *Bacillus licheniformis* | L-threonine 3-dehydrogenase | Q65JE7 |
| *Arabidopsis thaliana* | Alcohol dehydrogenase 6 | Q9SK86 |
| *Aspergillus fumigatus* | L-threonine 3-dehydrogenase | B0YC65 |
| *Saccharomyces cerevisiae* | Alcohol dehydrogenase-like 1 | P32771 |
| *Staphylococcus aureus* | Probable D-xylulose reductase A | Q6GBM4 |
| *Staphylococcus aureus* | S-(hydroxymethyl)glutathione dehydrogenase | Q7A742 |
| *Hypocrea jecorina* | General stress protein 69 | Q0GYU4 |
| *Aspergillus oryzae* | Alcohol dehydrogenase | Q86ZV0 |
| *Aspergillus clavatus* | Alcohol dehydrogenase | A1CFY8 |
| *Sulfolobus tokodaii* | D-xylulose reductase A | Q96XE0 |
| *Neosartorya fischeri* | Probable D-xylulose reductase A | A1D9C9 |
| *Metallosphaera sedula* | NAD-dependent alcohol dehydrogenase | A4YGN0 |
| *Sulfolobus* sp | Probable D-xylulose reductase A | P50381 |

TABLE 1-continued

Possible candidates for NADPH dependent HAR enzymes:

| Organism | Function | UNIPROT |
|---|---|---|
| Bacillus subtilis | Succinate-semialdehyde dehydrogenase (acetylating) | Q06004 |
| Escherichia coli | NAD-dependent alcohol dehydrogenase | P77280 |
| Saccharomyces cerevisiae | Sorbitol dehydrogenase | Q07993 |
| Thermococcus kodakarensis | Uncharacterized zinc-type alcohol dehydrogenase-like protein | Q5JI69 |
| Methylobacter marinus | D-xylulose reductase | P47734 |
| Bacillus subtilis | Probable L-threonine 3-dehydrogenase | O35045 |
| Bacillus subtilis | S-(hydroxymethyl)glutathione dehydrogenase | O06012 |
| Schizosaccharomyces pombe | Uncharacterized zinc-type alcohol dehydrogenase-like protein | Q9P6I8 |
| Dunaliella salina | Dihydroxyacetone reductase | B8Y210 |
| Escherichia coli | Uncharacterized zinc-type alcohol dehydrogenase-like protein | P75691 |
| Mycobacterium tuberculosis | Zinc-type alcohol dehydrogenase-like protein | O07737 |
| Saccharomyces cerevisiae | Aldehyde reductase | Q04894 |
| Streptomyces tenebrarius | Probable zinc-binding alcohol dehydrogenase | Q2MF22 |
| Escherichia coli | NADP-dependent alcohol dehydrogenase 6 | P27250 |
| Bacillus subtilis | 2-deoxy-scyllo-inosamine dehydrogenase | P80874 |

In this embodiment of the invention, the gene encoding a NADPH HAR overexpressed in the recombinant microorganism encodes a NADPH dependent acetol reductase chosen among the proteins listed above. From Uniprot number, the man skilled in the art is able to obtain number and sequence of corresponding gene. Preferentially, the microorganism of the invention expresses at least one gene coding for a NADPH dependent acetol reductase (NADPH HAR gene) having at least 60%, preferably at least 70%, more preferably at least 85% and even more preferably at least 90% amino acids identity with complete protein encoded by genes adh from *Clostridium beijerinckii* or adh from Thermoanaerobacter brockii or adh1 from *Entamoeba histolytica* or GOX1615 from *Gluconobacter oxydans* or gld2 from *Hypocrea jecorina* or yhdN from *Bacillus subtilis*. More preferentially, the microorganism of the invention expresses a gene chosen among adh from *Clostridium beijerinckii* or adh from *Thermoanaerobacter brockii* or adh1 from *Entamoeba histolytica* or GOX1615 from *Gluconobacter oxydans* r gld2 from *Hypocrea jecorina* or yhdN from *Bacillus subtilis* (i.e. 100% amino acids sequence identity with the protein sequence encoded by said genes). Even more preferentially, the NADPH dependent acetol reductase is encoded by adh gene from *Clostridium beijerinckii*.

Sequence identity between amino acid sequences can be determined by comparing a position in each of the sequences which may be aligned for the purposes of comparison. When a position in the compared sequences is occupied by the same amino acid, then the sequences are identical at that position. A degree of sequence identity between proteins is a function of the number of identical amino acid residues at positions shared by the sequences of said proteins.

To determine the percentage of identity between two amino acid sequences, the sequences are aligned for optimal comparison. For example, gaps can be introduced in the sequence of a first amino acid sequence for optimal alignment with the second amino acid sequence. The amino acid residues at corresponding amino acid positions are then compared. When a position in the first sequence is occupied by the same amino acid residue as the corresponding position in the second sequence, the molecules are identical at that position.

The percentage of identity between the two sequences is a function of the number of identical positions shared by the sequences. Hence % identity=number of identical positions/total number of overlapping positions×100.

Optimal alignment of sequences may be conducted by the global homology alignment algorithm of Needleman and Wunsch (1970), by computerized implementations of this algorithm or by visual inspection. The best alignment (i.e., resulting in the highest percentage of identity between the compared sequences) generated by the various methods is selected.

In other words, the percentage of sequence identity is calculated by comparing two optimally aligned sequences, determining the number of positions at which the identical amino acid occurs in both sequences to yield the number of matched positions, dividing the number of matched positions by the total number of positions and multiplying the result by 100 to yield the percentage of sequence identity.

In another preferred embodiment of the invention, NADPH HAR activity is enhanced by increasing NADPH dependent HAR activity as described above and/or by decreasing NADH dependent HAR activity.

Decreasing the activity of an enzyme means either decreasing its specific catalytic activity by mutating the gene so as to change the amino acid sequence and/or decreasing concentrations of the protein in the cell by mutating the nucleotidic sequence or by deleting the coding region of the gene.

In the present invention, decrease in NADH dependent HAR activity was performed by deleting the gldA gene, or by performing cofactor engineering on GldA enzyme, which resulted both in a decrease of NADH dependent HAR activity and in an increase of NADPH dependent HAR activity.

Therefore, the microorganism of the invention preferably overexpresses a mutant gldA*gene coding for a NADPH dependent glycerol dehydrogenase and/or is deleted in endogenous gldA gene.

Cofactor engineering means changing the cofactor specificity of an enzyme by replacing some specific amino acid residues in GldA protein. These resulted mutants (GldA*NADPH) are NADPH dependent and are different from GldA*mutant (GldA*A160T) disclosed above which is NADH dependent. The residues governing cofactor specificity in the cofactor-binding pocket known as the 'Rossman fold' have been thoroughly studied (Scrutton et al., 1990; Clermont et al., 1993; Corbier et al., 1990; Wu et al., 2012)

and the man skilled in the art is able to define which amino acid residues to modify in order to change cofactor specificity. Cofactor engineering has recently been successful in altering enzymes to prefer NADH as a cofactor instead of NADPH. An example is the enzyme Gre2p, an NADPH-preferring dehydrogenase found in *Saccharomyces cerevisiae*, which was modified by direct mutagenesis to have a decreased dependency on NADPH, and an increased affinity for NADH (Katzberg et al., 2010).

In the present invention a tri-dimensional structure model of GldA from *E. coli* was built from the tri-dimensional structure of the enzyme from *Bacillus stearothermophilus* (Ruzheinikov et al., 2001). The man skilled in the art knows how to build tri-dimensional homology models using for example a software such as Discovery Studio (Accelrys). Such models are useful for determining which amino acid residues to mutate in order to achieve the desired change in cofactor specificity. From the tri-dimensional structure of GldA from *E. coli* the inventors have identified amino acid residues to be replaced by a different amino acid residue at the same position:

D37
F39
V40
F43
T116
P161
L164

According to the invention, the change in GldA cofactor specificity is mediated by at least one mutation at position D37. In a preferred embodiment, the amino acid residue at position D37 is replaced by a glycine (D37G), an alanine (D37A) or a valine (D37V). In a most preferred embodiment, the amino acid residue at position D37 is replaced by a glycine (D37G).

In a preferred embodiment, the change in GldA cofactor specificity is improved by combining a mutation at position D37 with at least one mutation at position P161. Preferentially, the amino acid residue at position P161 is replaced by a serine (P161S) or a threonine (P161T). More preferentially, the amino acid residue at position P161 is replaced by a serine (P161S).

In a most preferred embodiment, the change in GldA cofactor specificity is improved by combining mutations at positions D37 and P161 with at least one mutation at position L164. Preferentially, the amino acid residue at position L164 is replaced by an alanine (L164A), a glycine (L164G) or a valine (L164V). More preferentially the amino acid residue at position L164 is replaced by an alanine (L164A).

In a specific embodiment, the microorganism of the invention overexpresses a mutant gldA*encoding GldA*mutant containing at least the following mutations: D37G, P161S and L164A.

In a preferred embodiment of the invention these mutations may be introduced in the GldA*mutant previously constructed and containing mutation A160T.

The amino acid sequenced of the glycerol dehydrogenase expressed by *E. coli* (strain K12) is publically available on the UniprotKB database under reference P0A9S5 (SEQ ID NO:28).

Hence, in order to enhance NADPH HAR dependent activity, the microorganism of the invention preferably overexpresses at least one gene coding for a NADPH dependent acetol reductase (NADPH HAR) as described above or a mutant gldA*gene coding for a NADPH dependent glycerol dehydrogenase as described above.

In other specific embodiments of the invention, the modified microorganism of the invention may:
overexpress at least one NADPH HAR gene and may be deleted in gldA gene,
overexpress at least one NADPH HAR gene and gldA*NADPH mutant, or
overexpress at least one NADPH HAR gene and gldA*NADPH mutant, and may be deleted in gldA gene.

In another aspect of the invention, the production of 1,2-propanediol is further improved by combining an increase in NADPH dependent HAR activity as described above with an increase in NADPH availability in the cell.

Strategies for increasing NADPH availability in the cell are well known from the man skilled in the art (reviewed in Lee et al., 2013). In the present invention, NADPH availability in the cell is increased by:
overexpressing the pntAB operon coding for the membrane-bound transhydrogenase (WO2012/055798A1), and/or
attenuating the pgi gene coding for a phosphoglucose isomerase, and/or
increasing the flux through the pentose phosphate pathway by decreasing the activity of the phosphofructokinase encoded by pfkA gene (WO2005/047498) and overexpressing the zwf gene coding for the glucose-6-phosphate dehydrogenase (Shin et al., 2002), and/or
overexpressing the gapN gene from *Streptococcus mutans* coding for the NADPH generating glyceraldehyde-3-phosphate (Centeno-Leija et al., 2013),
and/or overexpressing a mutant lpd*gene coding for a lipoamide dehydrogenase able to generate NADPH (Bocanegra et al., 1993),
and/or overexpressing the yjeF gene coding for an ADP-dependent dehydratase reactivating NADH(X) and NADPH(X) produced by enzymatic or heat-dependent hydration (Marbaix et al., 2011).

In a further aspect of the invention, when the microorganism of the invention overexpresses NADPH HAR gene, the yqhD gene coding for methylglyoxal reductase (MGR) has been deleted. Under such conditions, the HAR protein not only acts as a NADPH dependent HAR enzyme but also as a NADPH dependent MGR enzyme, carrying the two-step NADPH dependent reduction of methylglyoxal into 1,2-propanediol. Such activity may be carried out by any of the candidates for NADPH dependent HAR enzymes that have been listed above.

In a more preferred embodiment of the invention, the production of 1,2-propanediol in a fermentative process by a recombinant microorganism, wherein NADPH dependent acetol reductase activity is enhanced according to any of the modifications described above, from carbohydrate as carbon source, may be achieved through a combination of the above discussed modifications in said microorganism, for example:
expressions of at least one NADPH HAR gene and pntAB genes are enhanced,
expression of at least one NADPH HAR gene is enhanced and gldA gene is deleted,
expressions of at least one NADPH HAR gene and pntAB are enhanced whereas gldA gene is deleted,
expressions of at least one NADPH HAR gene and yjeF are enhanced whereas gldA gene is deleted,
expressions of at least one NADPH HAR gene is enhanced and pgi is attenuated whereas gldA gene is deleted, expressions of at least one NADPH HAR gene and zwf are enhanced whereas gldA gene and pfkA gene are attenuated, expressions of at least one NADPH HAR gene and gapN are enhanced whereas gldA gene is deleted, expressions of at least one NADPH HAR gene and lpd*mutant are enhanced whereas gldA gene is deleted expressions of a mutant GldA*NADPH encoding gene are enhanced and gldA gene is deleted, expressions of a mutant GldA*NADPH encoding gene and pntAB genes are enhanced, expressions of a mutant GldA*NADPH encoding gene and pntAB genes are enhanced whereas gldA gene is deleted.

expressions of at least one NADPH HAR gene is enhanced and yqhD gene is attenuated whereas gldA gene is deleted expressions of at least one NADPH HAR gene and pntAB genes are enhanced whereas yqhD gene and gldA gene are deleted.

EXAMPLES

Example 1: Methods

In the examples given below, methods well known in the art were used to construct *E. coli* strains containing replicating vectors and/or various chromosomal deletions, and substitutions using homologous recombination well described by Datsenko & Wanner, (2000) for *Escherichia coli*. In the same manner, the use of plasmids or vectors to express or overexpress one or several genes in a recombinant microorganisms are well known by the man skilled in the art. Examples of suitable *E. coli* expression vectors include pTrc, pACYC184n pBR322, pUC18, pUC19, pKC30, pRep4, pHS1, pHS2, pPLc236, etc. . . .

Several protocols have been used in the following examples. Protocol 1 (chromosomal modifications by homologous recombination, selection of recombinants), protocol 2 (transduction of phage P1) and protocol 3 (antibiotic cassette excision, the resistance genes were removed when necessary) used in this invention have been fully described in patent application EP 2532751. Chromosomal modifications were verified by a PCR analysis with appropriate oligonucleotides that the person skilled in the art is able to design.

Protocol 4: Construction of Recombinant Plasmids

Recombinant DNA technology is well described in the art. The DNA fragments and chosen plasmid were digested with compatible restriction enzymes (that the person skilled in the art will be able to define), then ligated and transformed into competent cells. Transformants were analysed and recombinant plasmids of interest were verified by DNA sequencing.

TABLE 2

Sequences cited in the following examples

| SEQ ID No | Sequence 5'→3' |
|---|---|
| 1 | cgtgcaaacctacaagccgatcttgccattgtaggcgccggtggc gcgggattacgtgctgcaattgctgccgcgcaggcCATATGAATA TCCTCCTTAG |
| 2 | CGTTAGATTGTAACGACACCAATCAGCGTGACAACTGTCAGGATA GCAGCCAGACCGTAGAAAACCCATTTGCCCGCAGGTGTAGGCTGG AGCTGCTTCG |
| 3 | ATGTTTAAGAATGCATTTGCTAACCTGCAAAAGGTCGGTAAATCG CTGATGCTGCCGGTATCCGTACTGCCTATCGCAGGtgtaggctgg agctgcttcg |
| 4 | TTAGTGGTTACGGATGTACTCATCCATCTCGGTTTTCAGGTTATC GGATTTAGTACCGAAAATCGCCTGAACACCAGAACcatatgaata tcctccttag |
| 5 | atggaccgcattattcaatcaccgggtaaatacatccagggcgct gatgtgattaatcgtctgggcgaatacctgaagccgtgtaggctg gagctgcttcg |
| 6 | TTATTCCCACTCTTGCAGGAAACGCTGACCGTACTGGTCGGCTAC CAGCAGAGCGGCGTAAACCTGATCTGGCGTCGCGCCATATGAATA TCCTCCTTAG |
| 7 | ATCCGGTATAGGAGGTATAGA |
| 8 | gaccgtcgaagacaattatcagtctttatccggcgttctaaggtg tttatcccactatcacggctgaatcgttaatattttgcgagttca cgccgaaatactgatttaggcgctagatcacaggcataatttca gtacgttatagggcgtttgttactaattttattttaacggagtaac atttagctcgtacatgagcagcttgtgtggctcctgacacaggca aaccatcatcaataaaaccgatggaagggaatatc |
| 9 | atgcgaattggcataccaagagaacggttaaccaatgaaacccgt gttgcagcaacgccaaaaacagtggaacagctgctgaaactgggt tttaccgtcgcggtagagagcggcgcgggtcaactggcaagattg acgataaagcgtagtgcaagcgggcgctgaaattgtagaagggaa tagcgtctggcagtcagagatcattctgaaggtcaatgcgccgtt agatgatgaaattgcgttactgaatcctgggac |
| 10 | AGACAATAATCGAACAACATATTAAGGAGAGTTT |
| 11 | ccaacgcagaccgctgcctggcaggcactacagaaacacttcgat gaaatgaaagacgttacgatcgccgatctttttgctgtaggctgg agctgcttcg |
| 12 | GCGCCACGCTTTATAGCGGTTAATCAGACCATTGGTCGAGCTATC GTGGCTGCTGATTTCTTTATCATCTTTCAGCTCTGCATATGAATA TCCTCCTTAG |
| 13 | gttcctcggttctgcgcgtttcccggaattccgcgacgagaacat ccgcgccgtggctatcgaaaacctgaaaaaacgtggtgtaggctg gagctgcttcg |
| 14 | GGCCTGATAAGCGAAGCGCATCAGGCATTTTTGCTTCTGTCATCG GTTTCAGGGTAAAGGAATCTGCCTTTTTCCGAAATCACATATGAA TATCCTCCTTAG |
| 15 | gttcctcggttctgcgcgtttcccggaattccgcgacgagaacat ccgcgccgtggctatcgaaaacctgaaaaaacgtgg |
| 16 | GGCCTGATAAGCGAAGCGCATCAGGCATTTTTGCTTCTGTCATCG GTTTCAGGGTAAAGGAATCTGCCTTTTTCCGAAATCA |
| 17 | AACTCATTTCGTTTTTAGGGAGGAATAA |
| 18 | CTTCCCCTTGAACGGGAGGGCATTTTTCTGAAATATCCTTTCTTT AGCCCATAATAATATTTCCTTTGCTGCGATTTTTTCAATTTCCGA TATATTCATAATTTATCAAGGTTGATATAAATATCAGTGAAGATC TCCAGATATTGTTGCGGAACTGGCTACGATAAAAGATAAATCAGA TGATGAATGGTGGCGTGCATTG |
| 19 | catcctgatgactggtgaactggcagcgttaattcaaaacctgat tgaaggattaggtggcgaagcacaacgttaattgctgattttcct ttaatgccggatgcgacgcctgccgcgtcttatccggcgtacgaa gccacaccaggcatataattattcgctacggcgagcaataattttt |

TABLE 2-continued

Sequences cited in the following examples

| SEQ ID No | Sequence 5'→3' |
|---|---|
| | tagcgcagcaatattatgcgttttacgctgtaacttgctccatgg acgttgtgtcattgtttacctcaagccg |
| 20 | ATGAGTACTGAAATCAAAACTCAGGTCGTGGTACTTGGGGCAGGC CCCGCAGGTTACTCCGCTGCCTTCCGTTGCGCTGACATATGAATA TCCTCCTTAG |
| 21 | TTACTTCTTCTTCGCTTTCGGGTTCGGCAGGTCGGTAATGCTACC TTCGAACACTTCTGCCGCCAGGCCCACAGACTCGTTGTAGGCTGG AGCTGCTTCG |
| 22 | TGGCAAGGTAAGCAAACTATAAGGAGGTCAAAT |
| 23 | aagctttgatggcaagcgataccattcgtattccgggtattgata caccgctgagccgtgttgcactgggcacctgggcaattggtggtt ggatgtggggtggtccggatgatgataatggtgttcgtaccattc atgcagcactggatgaaggtattaatctgattgataccgctccgg tttatggttttggtcatagcgaagaaattgttggtcgtgcactgg cagaaaaaccgaataaagcacatgttgcaaccaaactgggtctgc attgggttggtgaagatgagaaaaacatgaaagtgtttcgtgata gccgtccggcacgtattcgtaaagaagttgaagatagcctgcgtc gtctgcgtgttgaaaccattgatctggaacaaattcattggcctg atgataaaaccccgattgatgaaagcgcacgtgaactgcagaaac tgcatcaggatggtaaaattcgtgccctgggtgttagcaatttta gtccggaacaaatggatatattcgtgaagttgcaccgctggcaac cattcagcctccgctgaacctgtttgaacgtaccattgaaaaaga tattctgccgtatgccgaaaaacataatgcagttgttctggcata tggtgcactgtgtcgtggtctgctgaccggcaaaatgaatcgtga taccaccttttccgaaagatgatctgcctagcaatgatccgaaatt tcagaaaccgaacttcgagaaatatctggctgcaatgatgagtt tgaaaaactggccgagaaacgtggtaaaagcgttatggcatttgc agttcgttgggttctggatcaggggtccggttattgcactgtgggg tgcacgtaaaccgggtcaggttagcggtgttaaagatgtttaggt tggagcctgaccgacgaagaaaaaaaagcagttgatgatattctg gcacgtcatgttccgaatccgattgatccgacctttatggcaccg cctgcacgtgattaagaattc |
| 24 | aagctttgatggcctccaagacgtacactctgaacaccggtgcca agataccgcggtcgggttcggcacattcgccaatgagggtgcca agggcgagacatacgcagctgttacaaaggcactggacgttgagt accgccaccttgattgcgcgtggttttaccacaacgaagatgagg ttggtgacgcggtacgcgattactcgcccgccgacccgacgtgaa acgcgaggatctcttcatttgcaccaaagtaggaaccacctgcat gagccagaggacgtcaagtggagcgccaagaactcgtgcgaaaac ctcaaggtcgattacattgacctgttcctcgtccactggccaatc gcggccgagaagaacagcgacaggagcgtcaagctgggcccgat ggcaagtatgtcatcaaccaagccctgacggaaaacccagagcca acatggcgagccatggaagagcttgttgaaagcggcctcgtcaag gcaattggagtatccaactggacgattccgggggttgaagaagctc cttcagatcgccaagatcaagccggcagtgaaccagattgagatt cacccattcctaccaaacgaagagcttgtggcgttctgctagaga acgggatcctgcccgaagcctactcgccgctgggctcgcagaacc aggtcccaagcaccggcgagcgagtgcgcgacaaccccgacactca aagcggttgccgagcgaagcggctacagccttgcccagatcctat tggcatggggcctgaagcgaggatatgtggtcctcccaaagagct caactccaagccgtattgaaagcaacttcaacattccggagctga gtgatgaagactagagcgattcaacaggttgctaaggggagaca tactagatttgtcaacatgaaggacacgtaggatacaacgtttgg ccagaggaggaataagaattc |
| 25 | aagctttgactagtatgaaaggacttgctatgcttggaattggaa gaattggatggattgaaaagaaaatcccagaatgtggaccacttg atgcattagttagaccattagcacttgcaccatgtacatcagata cacataccgtttgggcaggagctattggagatagacatgatatga ttcttggacatgaaggcggttggacaaattgttaaagttggatcat tagttaagagattaaaagttggagataaagttattgtaccagcta ttacaccagattggggagaagaagaatcgcaaagaggatatccaa tgcattcaggaggaatgcttggaggatggaaattctcaaatttca aggatggagttttttcagaagttttccatgttaatgaagcagatg ccaatcttgcacttcttccaagagatattaaaccagaagatgcag ttatgttatcagatatggtaactactgattccatggagcagaat tagctaatattaaacttggagatactgtagtgttattggtattgg accagttggattaatgtcagttgcaggagcaaaccatcttggagc aggaagaatattgcagtaggatcaagaaaacattgttgtgatatt |

| SEQ ID No | Sequence 5'→3' |
|---|---|
| | gcattggaatatggagcaacagatattattaattataaaaatgga gatattgtagaacaaattcttaaagctacagacggcaaaggagtt gataaagtcgttattgcaggagggtgatgttcatacatttgcacaa gcagtcaaaatgattaaaccaggatcagatattggaaatgttaat tatcttggagaaggagataatattgatattccaagaagtgaatgg ggagttggaatgggtcataaacacattcatggaggtttaaccca ggtggaagagtcagaatggaaaaattagcatcacttatttcaact ggtaaattagatacttctaaacttattacacatagatttgaagga ttagaaaaagttgaagatgcattaatgttaatgaagaataaacca gcagaccttatcaaaccagttgtcagaattcattatgatgatgaa gatactcttcattaactcgag |
| 26 | atgaacaactttaatctgcacaccccaacccgcattctgtaggta aaggcgcaatcgctggtttacgcgaacaaattccgTGTAGGCTGG AGCTGCTTCG |
| 27 | ttagccgccgaactggtcaggatcgggaccgagacgcttgccctg atcgagttagcaatttcgccgagttcgtctttgCATATGAATATC CTCCTTAG |

Protocol 5: Evaluation of 1,2-propanediol Production Strains 1,2-propanediol production strains were cultivated in flask cultures as described in patent application EP 2532751, except that 20 g/L glucose or sucrose and 40 g/L MOPS were used. When necessary 100 µM IPTG was added to the medium. 1,2-propanediol (PG) and hydroxacetone (HA) were quantified by HPLC. The production of PG (gPG/L) and the conversion of HA to PG (gPG/L/(gHA/L+gPG/L)) give an estimate of strain performance for the production of 1,2-propanediol.

Protocol 6: Flask Cultures for the Production of Recombinant Proteins

Flask cultures for the production of recombinant proteins were carried out as described in patent application WO 2010/076324 except that the LB broth was supplemented with 5.0 g/L glucose.

Example 2: Construction of Strains 1, 2, 3 and 4

Construction of Strain 1

To inactivate the fumarate reductase flavoprotein complex encoded by the frdABCD operon and the glucose phosphotransferase Enzyme IIBC(Glc) encoded by the ptsG gene, the homologous recombination strategy was used (according to Protocols 1 and 3). Oligonucleotides for DfrdABCD: SEQ ID No 1 and 2 (listed in Table 2), and DptsG: SEQ ID No 3 and 4 (listed in Table 2), were used to PCR amplify the resistance cassettes. The strains retained were designated MG1655 DfrdABCD::Cm and MG1655 DptsG::Km. Finally, the DfrdABCD::Cm and the DptsG::Km deletions were transferred by P1 phage transduction (according to Protocol 2) into the evolved strain MG1655 lpd*DtpiA DpflAB DadhE DldhA DgloA DaldA DaldB Dedd DarcA Dndh described in patent application WO2008/116852, giving rise to strain 1.

Construction of Strain 2

The gldA*(A160T) gene was cloned into the pME101VB06 plasmid as described in patent application EP 2532751. This plasmid named pPG0078 was transformed into strain 1, giving rise to strain 2.

Construction of Strain 3

To express the triose phosphate isomerase encoded by the tpiA gene and to regulate the expression of the glyceraldehyde phosphate dehydrogenase encoded by the gapA gene, the homologous recombination strategy was used (according to Protocols 1 and 3). The tpiA gene was introduced as described in patent WO2008/116852 into the evolved strain MG1655 lpd*DtpiA DpflAB DadhE DldhA DgloA DaldA DaldB Dedd DarcA Dndh DfrdABCD. Then the genomic modification to regulate the gapA expression "CI857-PR01/RBS11-gapA" was introduced as described in patent EP 2532751 into the previous strain to give rise to strain 3.

Construction of Strain 4

To allow the growth of *Escherichia coli* on sucrose, the genes scrK, scrYAB and scrR from the plasmid pUR400 (Schmid et al., 1982) were cloned under their natural promoters on the plasmid pBBR1MCS3. This plasmid was named pPG0231. Plasmids pPG0078 and pPG0231 were transformed into strain 3, giving rise to strain 4.

Example 3: Production of 1,2-propanediol is Improved in Strains Overexpressing the Secondary Alcohol Dehydrogenase adh from *Clostridium beijerinckii*

Construction of Strain 5

The adh gene from *Clostridium beijerinckii* (Hanai et al., 2007) was cloned into the pME101VB01 plasmid described in patent application WO 2008/116853. This plasmid named pPG0468 was transformed into strain 1, giving rise to strain 5.

Construction of Strain 6

To inactivate the gldA gene, the homologous recombination strategy was used (according to Protocols 1 and 3). Oligonucleotides for DgldA: SEQ ID N° 5 and 6 (listed in Table 2), were used to PCR amplify the resistance cassette. The strain retained was designated MG1655 DgldA::Cm. The DgldA::Cm deletion was transferred by P1 phage transduction (according to Protocol 2) into strain 5, giving rise to strain 6.

Construction of Strain 7

Plasmids pPG0468 and pPG0231 were transformed into strain 3, giving rise to strain 7.

Construction of Strain 8

To inactivate the gldA gene, the DgldA::Cm deletion previously described was transferred by P1 phage transduction (according to Protocol 2) into strain 7, giving rise to strain 8.

Strains 5, 6, 7 and 8 expressing adh from *Clostridium beijerinckii* evaluated as described in Protocol 5 produced more 1,2-propanediol (PG) and had better conversion rates and yields compared to their respective controls strains 2 and 4 (Table 3).

TABLE 3

1,2-propanediol production by strains 5, 6, 7 and 8 expressing adh from *Clostridium beijerinckii*.

| Strain | Control strain | Culture conditions | PG | Conversion | Yield |
|---|---|---|---|---|---|
| 5 | 2 | Glucose 37° C. | + | + | + |
| 6 | 2 | Glucose 37° C. | ++ | ++ | ++ |
| 7 | 4 | Sucrose 37° C. | ++/+++ | ++/+++ | ++/+++ |
|   |   | Sucrose 30° C. | + | + | + |
| 8 | 4 | Sucrose 37° C. | ++++ | ++++ | ++++ |
|   |   | Sucrose 30° C. | + | + | + |

(The symbol ~ indicates that there is no significant difference between the strains, the symbol + indicates an increase between 10 to 100% in performance compared to the control strain, the symbol ++ indicates an increase between 100 to 200% compared to the control strain, the symbol +++ indicates an increase between 200 to 300% compared to the control strain and the symbol ++++ indicates an increase greater than 300% compared to the control strain):

Example 4: Production of 1,2-propanediol is Improved by Overexpressing the Pyridine Nucleotide Transhydrogenase pntAB in Strains Overexpressing the Secondary Alcohol Dehydrogenase adh from *Clostridium beijerinckii*

Construction of Strain 9

The native promoter region of pntAB was replaced by the inducible trc promoter (from the plasmid pTRC99A, Amersham Pharmacia) and the define ribosome binding site RBS120 (from RBS Calculator software) (SEQ ID No 7 listed in Table 2) using the homologous recombination strategy (according to Protocols 1 and 3). For chromosomal integration, a fragment carrying the artificial promoter region and a resistance marker both flanked by homologous DNA sequences to the targeted integration locus pntAB was PCR amplified by overlapping PCR technique (overlapping oligonucleotides). The sequences for recombination into pntAB are referred to as SEQ ID No 8 and 9 (listed in Table 2). The PCR product obtained was then introduced by electroporation into the strain MG1655 (pKD46). The strain retained was designated MG1655 Ptrc01/OP01/RBS120-pntAB::Cm. Then, the Ptrc01/OP01/RBS120-pntAB::Cm modification was transferred by P1 phage transduction (according to Protocol 2) into strain 6, giving rise to strain 9.

Construction of Strain 10

The Ptrc01/OP01/RBS120-pntAB::Cm modification previously described was transferred by P1 phage transduction (according to Protocol 2) into strain 8, giving rise to strain 10.

Strains 9 and 10 overexpressing pntAB evaluated as described in Protocol 5 produced more 1,2-propanediol (PG) and had better conversion rates and yields compared to strains 6 and 8, respectively (Table 4).

TABLE 4

1,2-propanediol production by strains 9 and 10 overexpressing pntAB.

| Strain | Control strain | Culture conditions | PG | Conversion | Yield |
|---|---|---|---|---|---|
| 6 | 2 | Glucose 37° C. | ++ | ++ | ++ |
| 9 | 2 | Glucose 37° C. | +++ | +++ | +++ |
| 8 | 4 | Sucrose 30° C. | + | + | + |
| 10 | 4 | Sucrose 30° C. | +++ | +++ | +++ |

(The symbol ~ indicates that there is no significant difference between the strains, the symbol + indicates an increase between 10 to 100% in performance compared to the control strain, the symbol ++ indicates an increase between 100 to 200% compared to the control strain, the symbol +++ indicates an increase between 200 to 300% compared to the control strain and the symbol ++++ indicates an increase greater than 300% compared to the control strain):

Example 5: Alternatives to the Overexpression of pntAB to Improve 1,2-propanediol Production in Strains Overexpressing the Secondary Alcohol Dehydrogenase adh from *Clostridium beijerinckii*

Construction of Strain 11

The yjeF gene from *Escherichia coli* was cloned in operon with adh under the define ribosome binding site RBS121 (from RBS Calculator software) (SEQ ID No 10 listed in Table 2) into the pPG0468 plasmid described in example 3. This plasmid was named pPG0518. Finally the plasmids pPG0518 and pPG0231 were transformed into the intermediate strain 8 (without plasmid) giving rise to strain 11.

Construction of Strain 12

To inactivate the pgi gene, the homologous recombination strategy was used (according to Protocols 1 and 3). Oligonucleotides for Dpgi: SEQ ID No 11 and 12 (listed in Table 2), were used to PCR amplify the resistance cassette. The strain retained was designated MG1655 Dpgi::Cm. The Dpgi::Cm deletion was transferred by P1 phage transduction (according to Protocol 2) into strain 8, giving rise to strain 12.

Construction of Strain 13

The native pfkA gene was replaced by the mutated pfkA*(L98Q) gene using the homologous recombination strategy (according to Protocols 1 and 3). First the pfkA gene was deleted using the oligonucleotides SEQ ID No 13 and 14 (listed in Table 2) to PCR amplify the resistance cassette. The strain retained was designated MG1655 DpfkA::Km. Then, for chromosomal integration, a fragment carrying the mutated pfkA*(L98Q) region and a resistance marker both flanked by homologous DNA sequences to the targeted integration locus pfkA was PCR amplified by overlapping PCR technique (overlapping oligonucleotides). The sequences for recombination into pfkA are referred to as SEQ ID No 15 and 16 (listed in Table 2). The PCR product obtained was then introduced by electroporation into the strain MG1655 DpfkA::Km (pKD46). The strain retained was designated MG1655 pfkA*(L98Q)::Cm. The pfkA*(L98Q)::Cm modification was transferred by P1 phage transduction (according to Protocol 2) into the intermediate strain 8 (strain without plasmid). The zwf gene from *Escherichia coli* was cloned in operon with adh under the define ribosome binding site RBS113 (from RBS Calculator software) (SEQ ID No 17 listed in Table 2) into the pPG0468 plasmid described in example 3. This plasmid was named pPG0532. Finally the plasmids pPG0532 and pPG0231 were transformed into the previous strain giving rise to strain 12.

Construction of Strain 14

To inactivate the gldA gene, the DgldA::Cm deletion previously described was transferred by P1 phage transduction (according to Protocol 2) into the intermediate evolved strain 3 (without gapA regulation). To express the NADP+-dependent glyceraldehyde 3-phosphate dehydrogenase from *Streptococcus mutans* encoded by the gapN gene, the homologous recombination strategy was used (according to Protocols 1 and 3). The gapA gene from *Escherichia coli* was replaced by the gapN gene from *Streptococcus mutans* as described by Centeno-Leija et al. (2013). The PCR product obtained was introduced by electroporation into the strain MG1655 (pKD46). The strain retained was designated MG1655 gapN::Cm. The gapN::Cm modification was transferred by P1 phage transduction (according to Protocol 2) into the previous strain. To chromosomally express the genes scrK, scrYAB and scrR, the homologous recombination strategy described by Datsenko & Wanner, 2000 (according to Protocols 1 and 3) was used. For chromosomal integration, a fragment carrying the genes scrK, scrYAB and scrR expressed under their natural promoters linked to a resistance marker both flanked by homologous DNA sequences to the targeted integration locus ykiA was PCR amplified by overlapping PCR technique (overlapping oligonucleotides). The sequences for recombination into ykiA are referred to as SEQ ID No 18 and 19 (listed in Table 2). The PCR products "DykiA::scrKYABR" obtained was then introduced by electroporation into the strain MG1655 (pKD46). The strain retained was designated MG1655 DykiA::scrKYABR::Cm. The DykiA::scrKYABR::Cm modification was transferred by P1 phage transduction (according to Protocol 2) into the previous strain. To allow the overproduction of the NADP+-dependent glyceraldehyde 3-phosphate dehydrogenase from *Streptococcus mutans*, the gapN gene was cloned on the pACYC184 plasmid as described by Centeno-Leija et al. (2013). This plasmid was named pPG0548. Finally the plasmids pPG0468 and pPG0548 were transformed into the previous strain giving rise to strain 13.

Construction of Strain 15

To inactivate the NAD+-dependent lipoamide dehydrogenase encoded by the lpd gene, the homologous recombination strategy was used (according to Protocols 1 and 3). Thus the oligonucleotides for Dlpd: SEQ ID N° 20 and 21 (listed in Table 2), were used to PCR amplify the resistance cassette. The strain retained was designated MG1655 Dlpd::Cm. Finally, the Dlpd::Cm deletion was transferred by P1 phage transduction (according to Protocol 2) into the intermediate strain 8, (strain without plasmid). The mutated lpd*(A55V/G185A/G189A/E203V/M204R/F205K/D206H/P210R) gene from *Escherichia coli* was PCR amplified by overlapping PCR technique (overlapping oligonucleotides) and cloned in operon with adh under the define ribosome binding site RBS131 (from RBS Calculator software) (SEQ ID No 22 listed in Table 2) into the pPG0468 plasmid described in example 3. This plasmid was named pPG0523. Finally the plasmids pPG0231 and pPG0523 were transformed into the previous strain giving rise to strain 14.

Strains 11, 12, 13, 14 and 15 evaluated as described in Protocol 5 produced more 1,2-propanediol (PG) and had better conversion rates compared to strain 8 (Table 5).

TABLE 5

1,2-propanediol production by strains 11, 12, 13, 14 and 15.

| Strain | Control strain | Culture conditions | PG | Conversion |
|---|---|---|---|---|
| 8 | 4 | Sucrose 30° C. | + | + |
| 11 | 4 | Sucrose 30° C. | ++ | ++ |
| 12 | 4 | Sucrose 30° C. | +++ | +++ |
| 13 | 4 | Sucrose 30° C. | +++ | +++ |
| 14 | 4 | Sucrose 30° C. | +++ | +++ |
| 15 | 4 | Sucrose 30° C. | +++ | +++ |

(The symbol ~ indicates that there is no significant difference between the strains, the symbol + indicates an increase between 10 to 100% in performance compared to the control strain, the symbol ++ indicates an increase between 100 to 200% compared to the control strain, the symbol +++ indicates an increase between 200 to 300% compared to the control strain and the symbol ++++ indicates an increase greater than 300% compared to the control strain):

Example 6: Alternatives to adh from *Clostridium beijerinckii*

Identification of Homologous Sequences and Construction of Phylogenetic Trees

The constructions of phylogenetic trees from a set of sequences were performed using the bioinformatics programs available on the website http://www.phylogeny.fr/ and the softwares are described in Dereeper et al. (2008) and Dereeper et al. (2010).

Step 1: Identification of Homologous Sequences

The identification of similar sequences was performed from secondary alcohol dehydrogenase family and aldehyde/ketone reductase family using the BLAST software by setting the following parameters: database (Swissprot/UNIPROT), e-value=0.01 and filter for low-complexity sequences.

Step 2: Construction of Phylogenetic Trees

Sequences were aligned with MUSCLE software and ambiguous regions were removed with Gblocks program. Then, the phylogenic tree was reconstructed using the maximum likelihood method implemented in the PhyML program. Graphical representation and edition of the phylogenetic tree were performed with TreeDyn.

TABLE 6

Candidates for NADPH dependent HAR enzymes:

| Organism | GI | UNIPROT |
|---|---|---|
| Clostridium_beijerinckii | 166228784 | P25984 |
| Thermoanaerobacter_brockii | 113443 | P14941 |
| Mycoplasma_pneumoniae | 2492770 | P75214 |
| Entamoeba_histolytica | 543776 | P35630 |
| Gadus_callarias | 113437 | P26325 |
| Photobacterium_damselae | 728805 | P39450 |
| Synechocystis_sp | 6225006 | P73138 |
| Oryza_sativa | 75339814 | Q4R1E8 |
| Hordeum_vulgare | 113385 | P10848 |
| Sparus_aurata | 5902742 | P79896 |
| Gadus_morhua | 5902740 | P81600 |
| Hordeum_vulgare | 113376 | P10847 |
| Zea_mays | 113377 | P04707 |
| Saccharomyces_cerevisiae | 586489 | P38230 |
| Pennisetum_glaucum | 113362 | P14219 |
| Oryctolagus_cuniculus | 3912977 | O46650 |
| Arabidopsis_thaliana | 122223583 | Q0V7W6 |
| Uromastyx_hardwickii | 1351882 | P25405 |
| Amycolatopsis_methanolica | 3915692 | P80094 |
| Zea_luxurians | 1351874 | Q07264 |
| Zea_mays | 113359 | P00333 |
| Oryctolagus_cuniculus | 3912976 | O46649 |
| Arabidopsis_thaliana | 148841208 | P06525 |
| Arabidopsis_thaliana | 158563847 | Q8LEB2 |
| Cupriavidus_necator | 113411 | P14940 |
| Rana_perezi | 113364 | P22797 |
| Arabidopsis_thaliana | 75337342 | Q9SK87 |
| Rattus_norvegicus | 48474724 | Q64563 |
| Malus_domestica | 1351887 | P48977 |
| Drosophila_melanogaster | 1168359 | P46415 |
| Mus_musculus | 338817905 | Q9QYY9 |
| Homo_sapiens | 308153684 | P08319 |
| Bacillus_subtilis | 3915097 | O31776 |
| Peromyscus_maniculatus | 1168352 | P41681 |
| Bacillus_licheniformis | 67461713 | Q65JE7 |
| Arabidopsis_thaliana | 75337341 | Q9SK86 |
| Aspergillus_fumigatus | 294863186 | B0YC65 |
| Saccharomyces_cerevisiae | 417769 | P32771 |
| Staphylococcus_aureus | 81827907 | Q6GBM4 |
| Staphylococcus_aureus | 81832555 | Q7A742 |
| Aspergillus_oryzae | 74696959 | Q86ZV0 |
| Aspergillus_clavatus | 294863185 | A1CFY8 |
| Sulfolobus_tokodaii | 74580971 | Q96XE0 |
| Neosartorya_fischeri | 294863179 | A1D9C9 |
| Metallosphaera_sedula | 353678127 | A4YGN0 |
| Sulfolobus_sp | 1703176 | P50381 |
| Bacillus_subtilis | 461928 | Q06004 |
| Escherichia_coli | 2492775 | P77280 |
| Saccharomyces_cerevisiae | 74655020 | Q07993 |
| Thermococcus_kodakarensis | 67461628 | Q5JI69 |
| Methylobacter_marinus | 221222447 | P47734 |
| Bacillus_subtilis | 81815843 | O35045 |
| Bacillus_subtilis | 251757237 | O06012 |
| Schizosaccharomyces_pombe | 74698317 | Q9P6I8 |
| Escherichia_coli | 2492774 | P75691 |
| Mycobacterium_tuberculosis | 81815028 | O07737 |
| Saccharomyces_cerevisiae | 2492777 | Q04894 |
| Streptomyces_tenebrarius | 94710637 | Q2MF22 |
| Escherichia_coli | 732035 | P27250 |
| Bacillus_subtilis | 3123233 | P80874 |
| Gluconobacter_oxydans | 81557013 | Q5FQJ0 |
| Hypocrea_jecorina | 121924008 | Q0GYU4 |
| Dunaliella_salina | 219107912 | B8Y210 |

Adh from *Clostridium beijerinckii* was most closely related to the *Thermoanaerobacterium brockii, Entamoeba histolytica* and Mycoplasma pneumoniae enzymes. The next best match was with alcohol dehydrogenases found in eukaryotes. Enzymes from *Gluconobacter oxydans, Hypocrea jecorina, Entamoeba histolytica* and *Bacillus subtilis* were cloned, purified and assayed for NADPH dependent hydroxyacetone reductase activity.

Construction of Strain 16

To inactivate the gldA gene, the homologous recombination strategy was used (according to Protocols 1 and 3). Oligonucleotides for DgldA: SEQ ID No 5 and 6 (listed in Table 2), were used to PCR amplify the resistance cassette. The strain retained was designated MG1655 DgldA::Km. Finally, the DgldA::Km deletion was transferred by P1 phage transduction (according to Protocol 2) into the strain BL21(DE3)star. To characterize the glycerol dehydrogenase from *Gluconobacter oxydans*, the synthetic gene gld optimized for *Escherichia coli* (SEQ ID No 23 listed in table 2) was cloned into the expression plasmid pPAL7 (Biorad®). This plasmid was named pPG0381 and transformed into strain BL21(DE3)star DgldA::Km, giving rise to strain 16.

Construction of Strain 17

To characterize the glycerol dehydrogenase from *Hypocrea jecorina*, the synthetic gene gld2 optimized for *Escherichia coli* (SEQ ID No 24 listed in table 2) was cloned into the expression plasmid pPAL7 (Biorad®). This plasmid was named pPG0418 and transformed into strain BL21(DE3)star DgldA::Km previously described giving rise to strain 17.

Construction of Strain 18

To characterize the alcohol dehydrogenase from *Entamoeba histolytica*, the synthetic gene adh1 optimized for *Escherichia coli* (SEQ ID No 25 listed in table 2) was cloned into the expression plasmid pPAL7 (Biorad®). This plasmid was named pPG0539 and transformed into strain BL21 (DE3)codonplus, giving rise to strain 18.

Construction of Strain 19

To characterize the aldo keto reductase from *Bacillus subtilis*, the gene yhdN from *Bacillus subtilis* was cloned into the expression plasmid pPAL7 (Biorad®). This plasmid was named pPG0357 and transformed into strain BL21 (DE3), giving rise to strain 19.

Recombinant Protein Purification

Strains 16, 17, 18 and 19 were cultivated as described in Protocol 6. Cells (350-500 mg dry weight) were resuspended in extraction buffer (60-90 ml) with protease inhibitor cocktail. The suspended cells were disrupted by six sonication cycles of 30 sec on ice (Branson sonifier, 70 W) followed by incubating for 1 hour at room temperature with 1 mM MgCl2 and 2 UI/ml of DNaseI. Cell debris were removed by centrifugation at 12000 g for 30 min at 4° C. The supernatant was kept as the crude cell-extract. Recombinant protein was purified from the crude extract by using subtilisine affinity chromatography (PROfinity EXact Cartridge 5 ml, BIORAD) according to the manufacturer's instructions. Fractions containing the protein were pooled, concentrated and loaded onto a gel filtration column (Superdex 200 10/300 GL column, GE Healthcare). Protein concentration was determined using Bradford assay.

NADPH Dependent Hydroxyacetone Reductase (HAR NADPH) of Purified Enzymes

HAR NADPH activity was determined by measuring the consumption of NADPH at 340 nm on a spectrophotometer ($\varepsilon_{340nm}$=6290 $M^{-1}$ $cm^{-1}$) and at 30° C. The reaction mixture (1 mL) containing assay buffer, 0.2 mM NADPH and purified protein was incubated for 5 min at 30° C. Then, 30 mM hydroxyacetone was added to start the reaction. One unit of enzyme activity was defined as the amount of enzyme catalyzing the decrease of 1 μmol of NADPH per min. Specific enzyme activity was expressed as units of enzyme activity per mg of protein. The activity value determined without hydroxyacetone was subtracted.

TABLE 7

HAR NADPH dependent activity for specific candidates:

| Enzyme | Assay buffer | HAR NADPH (mUI/mg) |
|---|---|---|
| Gld | 20 mM Hepes (pH 7.5) | 5461 |
| Gld2 | 10 mM sodium phosphate (pH 7) | 9623 |
| Adh1 | 50 mM Tris-HCl (pH 7.5) | 13325 |
| YhdN | 20 mM Tris-HCl (pH 7.5) | 1975 |

Construction of Strain 20

The optimized adh1 gene from *Entamoeba histolytica* was cloned into the pME101VB01 plasmid described in patent application WO 2008/116853. This plasmid was named pPG0544. Plasmids pPG0544 and pPG0231 were transformed into strain 3 described in Example 2, then the gldA gene was inactivated as described in Example 3 and the pntAB operon was overexpressed as described in Example 4, giving rise to strain 19.

Strain 20 evaluated as described in Protocol 5 produced more 1,2-propanediol (PG) and had a better conversion rate compared to strain 4 (Table 8).

TABLE 8

1,2-propanediol production by strain 20 expressing adh1 gene from *Entamoeba histolytica*.

| Strain | Control strain | Culture conditions | PG | Conversion |
|---|---|---|---|---|
| 20 | 4 | Sucrose 37° C. | +++ | +++ |

(The symbol ~ indicates that there is no significant difference between the strains, the symbol + indicates an increase between 10 to 100% in performance compared to the control strain, the symbol ++ indicates an increase between 100 to 200% compared to the control strain, the symbol +++ indicates an increase between 200 to 300% compared to the control strain and the symbol ++++ indicates an increase greater than 300% compared to the control strain):

Example 7: Co-Factor Refactoring of GldA*(A160T)

Enzyme Design and Structural Analysis

Homology models of GldA*(A160T) were built from the X-ray structure of a glycerol dehydrogenase of *Bacillus stearothermophilus*. The models were calculated by using the Discovery Studio software (Accelrys). These models were compared with the structure of NAD and NADP dependent enzymes which had at least 30% identity and whose structure was known.

Amino acids involved in cofactor specificity were identified through sequence alignment between the sequence of GldA*(A160T) and several NAD and NADP dependent dehydrogenases, superimposition between the homology models of GldA*(A160T) and the glycerol dehydrogenases present in the RCSB Protein Data Bank, and comparison with data found in Clermont et al. (1993), Ruzheinikov et al. (2001), Corbier et al. (1990) and Wu et al. (2012).

Two mutants were defined from the sequential and structural analysis: D37G and D37G/P161S/L164A.

Construction of Strain 21

To characterize the mutated 1,2-propanediol:NAD+ oxidoreductase from *Escherichia coli*, first the gene gldA was cloned into the expression plasmid pET101/D-TOPO (Lifetechnologies®). This plasmid was named pPG0029. To overexpress the mutated gldA*(A160T) gene, site-directed mutagenesis on pPG0029 was used. This plasmid was named pPG0394 and transformed into strain BL21(DE3)star DgldA::Km, giving rise to the strain 21.

Construction of Strain 22

To overexpress the mutated gldA*(A160T/D37G) gene, site-directed mutagenesis on pETTOPO-gldA*(A160T) was used. This plasmid was named pPG0425 and transformed into strain BL21(DE3)star DgldA::Km, giving rise to the strain 22.

Construction of Strain 23

To overexpress the mutated gldA*(A160T/D37G/P161S/L164A) gene, site-directed mutagenesis on pPG0425 was used. This plasmid was named pPG0438 and transformed into strain BL21(DE3)star DgldA::Km, giving rise to the strain 23.

Purification of GldA*(A160T), GldA*(A160T/D37G) and GldA*(A160T/D37G/P161S/L164A)

Strains 21, 22 and 23 were cultivated as described in Protocol 6. Cells (500 mg dry weight) were resuspended in 90 mL of extraction buffer (100 mM potassium phosphate pH 7.6, 20 mM imidazole and protease inhibitor cocktail). The suspended cells were disrupted by 8 sonication cycles of 30 sec on ice (Branson sonifier, 70 W) followed by an incubation for 45 min at room temperature with 5 mM MgCl2 and 2 UI/ml of DNaseI. Cell debris were removed by centrifugation at 12000 g for 30 min at 4° C. The supernatant was kept as the crude extract. The enzymes were purified from the crude extract by using Nickel affinity chromatography (HisTrapFF 1 mL, GE Healthcare) according to the manufacturer's instructions. The enzymes were eluted by using a linear gradient of imidazole (20 to 500 mM) in 100 mM potassium phosphate (pH 7.6). After a desalting step by gel filtration (Superdex200 10/300 GL column, GE Healthcare) equilibrated with 100 mM MES-KOH (pH 6.5), protein concentrations were determined using Bradford assay.

Characterization of GldA*(A160T), GldA*(A160T/D37G) and GldA*(A160T/D37G/P161S/L164A)

NADPH dependent hydroxyacetone reductase activity (HAR NADPH) was determined by measuring the consumption of NADPH at 340 nm on a spectrophotometer ( L$_{340}$=6290 M$^{-1}$ cm$^{-1}$) and at 30° C. The reaction mixture (1 mL) containing 100 mM MES-KOH (pH 6.5), 0.1 mM FeSO4, 30 mM ammonium sulfate, 0.05 to 0.4 mM NADPH and purified enzyme was incubated for 5 min at 30° C. Then, 0.1 to 10 mM hydroxyacetone was added to start the reaction. The NADH dependent hydroxyacetone reductase (HAR NADH) assay is performed under the same conditions that HAR NADPH except that NADPH was replaced by NADH in the reaction mixture and the activity was determined by measuring the consumption of NADH at 340 nm. Kinetic parameters were determined with Sigmaplot by fitting to the Michaelis-Menten equation.

GldA*(A160T/D37G) and GldA*(A160T/D37G/P161S/L164A) enzymes showed increased catalytic efficiencies with NADPH and decreased catalytic efficiencies with NADH compared to GldA*(A160T) (Table 9).

TABLE 9

Catalytic efficiencies of GldA* NADPH mutants:

| Enzyme | GldA* (A160T) | GldA* (A160T/D37G) | GldA* (A160T/D37G/P161S/L164A) |
|---|---|---|---|
| Kcat/Km NADPH (mM−1s−1) | 10 | 177 | 168 |
| Kcat/Km NADH (mM−1s−1) | 98 | 61 | 41 |

Construction of Strain 24

The mutated gldA*(A160T/D37G/P161S/L164A) gene was cloned into the pME101 derived plasmid as described for the construction of pME101VB06-gldA*(A160T) in patent application EP 2532751. This plasmid was named pPG0467. Finally the plasmids pPG0467 and pPG0231 were transformed into the intermediate strain 8 (strain without plasmid) described in example 2, giving rise to strain 24.

Strain 24 evaluated as described in Protocol 5 produced more 1,2-propanediol (PG) and had a better conversion rate compared to strain 4 (Table 10).

TABLE 10

1,2-propanediol production by strain 24.

| Strain | Control strain | Culture conditions | PG | Conversion |
|---|---|---|---|---|
| 24 | 4 | Sucrose 37° C. | +++ | ++ |

(The symbol ~ indicates that there is no significant difference between the strains, the symbol + indicates an increase between 10 to 100% in performance compared to the control strain, the symbol ++ indicates an increase between 100 to 200% compared to the control strain, the symbol +++ indicates an increase between 200 to 300% compared to the control strain and the symbol ++++ indicates an increase greater than 300% compared to the control strain):

Example 8: MG=>PG Activity by Adh from *Clostridium beijerinckii*

Construction of Strain 25

The optimized adh gene from *Clostridium beijerinckii* (Hanai, Atsumi and Liao, 2007) was cloned into the expression plasmid pET28a. This plasmid was named pPG0445 and transformed into strain BL21(DE3), giving rise to strain 25.

Purification of Adh from *Clostridium beijerinckii*

Strain 25 was cultivated as described in Protocol 6. Cells (315 mg dry weight) were resuspended in 50 mL of extraction buffer (20 mM Tris-HCl pH 7.3, 0.1 mM DTT, 0.1 mM benzamidine, 10% glycerol, 0.02% sodium azide and protease inhibitor cocktail). The suspended cells were disrupted by 8 sonication cycles of 30 sec on ice (Branson sonifier, 70 W). Cell debris were removed by centrifugation at 12000 g for 30 min at 4° C. The supernatant was exposed to heat (65° for 5 min) and then recentrifuged at 12000 g for 30 min at 4° C. The protein was purified from the supernatant by using Nickel affinity chromatography (HisTrapFF 1 mL, GE Healthcare) according to the manufacturer's instructions. The protein was eluted by using a linear gradient of imidazole (20 to 500 mM) in 50 mM Tris-HCl (pH 7.4). The fractions which contain the protein were pooled, concentrated and dialysed against 50 mM Tris-HCl (pH 7). Protein concentration was determined using Bradford assay.

Quantification of 1,2-propanediol Produced from Methylglyoxal 5-10 µg of purified enzyme was incubated for 30 min at 30° C. in 50 mM Tris-HCl (pH7.5), 10 mM methylglyoxal and 5 mM NADPH. The quantity of 1,2-propanediol produced by Adh from methylglyoxal was measured directly by GC-MS (Agilent Technologies).

Under such conditions 4.6 mM of 1,2-propanediol were produced while no 1,2-propanediol was produced when either methylglyoxal or enzyme were omitted.

Construction of Strains 26, 27 and 28

To inactivate the gldA gene, the DgldA::Km deletion previously described and the tpiA gene were co-transferred by P1 phage transduction (according to Protocol 2) into the strain MG1655 lpd*DtpiA DpflAB DadhE DldhA DgloA DaldA DaldB Dedd described in patent application WO2008/116852. The genomic modification to regulate the gapA expression "CI857-PR01/RBS11-gapA" was introduced as described in patent EP 2532751 into the previous strain. To inactivate the aldehyde reductase encoded by the yqhD gene and the glyoxal reductase encoded by the yqhE gene, the homologous recombination strategy was used (according to Protocols 1 and 3). Oligonucleotides for DyqhDE: SEQ ID No 26 and 27 (listed in Table 2) were used to PCR amplify the resistance cassettes. The strain retained was designated MG1655 DyqhDE::Bs. The DyqhDE::Bs deletion was transferred by P1 phage transduction (according to Protocol 2) into the previous strain, giving rise to strain 26. Then the plasmid pPG0468 was transformed into this strain, giving rise to strain 27. Finally the Ptrc01/OP01/RBS120-pntAB:: Cm modification previously described was transferred by P1 phage transduction (according to Protocol 2) into strain 27, giving rise to strain 28.

When evaluated as described in Protocol 5 strains 27 and 28 produced more 1,2-propanediol (PG) than strain 26.

REFERENCES

Altaras N E and Cameron D C (2000), Biotechnol. Prog., 16: 940-946

Altaras N E and Cameron D C (1999), Appl. Environ. Microbiol., 65: 1180-1185

Badia J, Ros J, Aguilar J (1985), *J. Bacteriol.* 161: 435-437

Berrios-Rivera S J, San K Y, Bennett G N (2003), J. Ind. Microbiol. Biotechnol., 30: 34-40

Bocanegra J, Scrutton N, Perham R (1993) Biochemistry, 32 (11): 2737-2740

Cameron D C, Altaras N E, Hoffman M L, Shaw A J (1998), Biotechnol. Prog., 14: 116-125

Carrier T & Keasling J (1999), Biotechnol Prog., 15 (1): 58-64

Centeno-Leija S, Utrilla J, Flores N, Rodriguez A, Gosset G, Martinez A (2013) Antonie Van Leeuwenhoek., 104 (6), 913-924.

Clermont S, Corbier C, Mely Y, Gerard D, Wonacott A, Branlant G, (1993), Biochemistry, 32 (38): 10178-10184

Corbier C, Clermont S, Billard P, Skarzynski T, Branlant C, Wonacott A, Branlant G (1990), Biochemistry, 29 (30): 7101-7106

Datsenko K A & Wanner B L, (2000), *Proc Natl Acad Sci USA.*, 97: 6640-6645

Dereeper A, Audic S, Claverie J, Blanc G (2010), BMC Evol Biol., 12: 10:8

Dereeper A, Guignon V, Blanc G, Audic S, Buffet S, Chevenet F, Dufayard J, Guindon S, Lefort V, Lescot M, Claverie J, Gascuel O (2008) Nucleic Acids Res., 1: 36 (Web Server issue):W465-9. Epub 2008 Apr. 19

Fuhrer T and Sauer U (2009), J. Bacteriol., 191 (7): 2112-2121

Hanai T, Atsumi S, Liao J (2007), Appl. Environ. Microbiol., 73: 7814-7818

Huang K, Rudolph F B, Bennett G N (1999), Appl. Environ. Microbiol., 65: 3244-3247

Ismaiel A, Zhu C, Colby G, Chen J (1993), J Bacteriol., 175 (16): 5097-5105

Jarboe L R (2011), Appl Microbiol Biotechnol., 89: 249-257.

Katzberg M, Skorupa-Parachin N, Gorwa-Grauslund M, Bertau M (2010), Int. J. Mol. Sci., 11(4): 1735-1758

Kelley J & Dekker E (1984), J Biol Chem., 259 (4): 2124-2129

Lee S, McCormick M, Lippard S, Cho U (2013), Nature, 494: 380-384

Li H and Liao J (2013), Microb Cell Fact., 12 (1): 4

Marbaix A, Noel G, Detroux A, Vertommen D, Schaftingen E, Linster C (2011), J Biol Chem., 286 (48), 41246-41252

Needleman and Wunsch (1970), J. Mol. Biol., 48(3), 443-453

Old S E, Sato S, Kador P F, Carper D A (1990), Proc Natl Acad Sci USA., 87: 4942-4945

Ruzheinikov S, Burke J, Sedelnikova S, Baker P, Taylor R, Bullough P, Muir N (2001), Structure, 9 (9): 789-802

Salis H (2011), Methods Enzymol., 498:19-42

Schmid K, Schupfner M, Schmitt R (1982), J. Bacteriol., 151: 68-76

Segel I (1993), Enzyme kinetics, John Wiley & Sons, pp. 44-54 and 100-112

Scrutton N, Berry An Perham R (1990), Nature, 343: 38-43

Lim S, Jung Y, Shin H, Lee Y (2002), J Biosci Bioeng., 93 (6):543-549

Wu C, Hwa Y, Chen Y, Lim C (2012), J Phys Chem B, 116 (19): 5644-5652

The invention claimed is:

1. A method for the production of 1,2-propanediol in a fermentative process comprising the steps:
culturing an *E. coli* microorganism genetically modified for the production of 1,2-propanediol in an appropriate culture medium comprising a carbohydrate as a source of carbon, and
recovering 1,2-propanediol from said culture medium, wherein said *E. Coli* microorganism expresses
a *Clostridium beijerinckii* adh gene coding for a NADPH dependent acetol reductase or
a gldA gene coding for a NADPH dependent glycerol dehydrogenase having at least 90% sequence identity to the sequence set forth in SEQ ID NO:28, wherein the dehydrogenase comprises a glycine, an alanine, or a valine at the amino acid residue corresponding to position 37 of SEQ ID NO: 28.

2. The method of claim 1, wherein a NADPH availability is increased in the microorganism by at least one of the following genetic modifications:
a pntAB gene operon coding for a nicotinamide nucleotide transhydrogenase is overexpressed, and/or
a pgi gene coding for a phosphoglucose isomerase is attenuated, and/or
a pfkA gene coding for a phosphofructokinase is attenuated, and/or
a zwf gene coding for a glucose-6-phosphate dehydrogenase is overexpressed, and/or
a yjeF gene coding for an ADP-dependent dehydratase is overexpressed, and/or
a gapN gene coding for a NADP-dependent glyceraldehyde-3-phosphate dehydrogenase is overexpressed, and/or
a mutant lpd* gene coding for a NADP-dependent lipoamide dehydrogenase is overexpressed.

3. The method of claim 1, wherein an endogenous gldA gene coding for an endogenous NADH dependent glycerol dehydrogenase is deleted in the microorganism.

4. The method of claim 1, wherein the microorganism further comprises a deletion of a yqhD gene coding for a methylglyoxal reductase.

5. The method of claim 1, wherein said genetically modified microorganism overexpresses the gldA gene coding for the GldA NADPH dependent glycerol dehydrogenase having at least 90% sequence identity to the sequence set forth in SEQ ID NO: 28, wherein the dehydrogenase further comprises a serine or a threonine at the amino acid residue corresponding to position 161 of SEQ ID NO: 28.

6. The method of claim 1, wherein said genetically modified microorganism overexpresses the gldA gene coding for the GldA NADPH dependent glycerol dehydrogenase having at least 90% sequence identity to the sequence set forth in SEQ ID NO: 28, wherein the dehydrogenase further comprises an alanine, a glycine, or a valine at the amino acid residue corresponding to position 164 of SEQ ID NO: 28.

7. The method of claim 1, wherein said genetically modified microorganism overexpresses the gldA gene coding for the GldA NADPH dependent glycerol dehydrogenase having at least 90% sequence identity to the sequence set forth in SEQ ID NO: 28, wherein the dehydrogenase further comprises a threonine at the amino acid residue corresponding to position 160 of SEQ ID NO: 28.

8. The method of claim 1, wherein said genetically modified microorganism overexpresses the gldA gene coding for the GldA NADPH dependent glycerol dehydrogenase having at least 90% sequence identity to the sequence set forth in SEQ ID NO: 28, wherein the dehydrogenase further comprises a serine at the amino acid residue corresponding to position 161 of SEQ ID NO: 28 and an alanine at the amino acid residue corresponding to position 164 of SEQ ID NO: 28.

9. The method of claim 1, wherein said genetically modified microorganism overexpresses the gldA gene coding for the GldA NADPH dependent glycerol dehydrogenase having at least 90% sequence identity to the sequence set forth in SEQ ID NO: 28, wherein the dehydrogenase further comprises a serine at the amino acid residue corresponding to position 161 of SEQ ID NO: 28, an alanine at the amino acid residue corresponding to position 164 of SEQ ID NO: 28, and a threonine at the amino acid residue corresponding to position 160 of SEQ ID NO: 28.

10. The method of claim 1, wherein the microorganism further comprises the genes scrK, scrYAB and scrR.

11. The method of claim 1, wherein the source of carbon is derived from renewable feed-stock.

12. The method of claim 1, wherein the carbohydrate is selected among the group consisting of glucose, fructose, mannose, xylose, arabinose, galactose, sucrose, cellobiose, maltose, lactose, raffinose, stachyose, maltodextrins, cellulose, hemicellulose, starch, methanol, formaldehyde and glycerol.

13. The method of claim 12, wherein the carbohydrate is glucose or sucrose.

* * * * *